US012646603B2

(12) United States Patent
Malej et al.

(10) Patent No.: US 12,646,603 B2
(45) Date of Patent: Jun. 2, 2026

(54) BRAIN STIMULATION SYSTEM, DEVICE, ARRANGEMENT AND CORRESPONDING METHOD FOR TREATING APHASIA

(71) Applicant: Neuro Device Group S.A., Warsaw (PL)

(72) Inventors: Krzysztof Mateusz Malej, Warsaw (PL); Pawel Sebastian Soluch, Warsaw (PL); Mateusz Marek Orzechowski, Warsaw (PL); Justyna Julia Garnier, Warsaw (PL)

(73) Assignee: Neuro Device Group S.A., Warsaw (PL)

( * ) Notice: Subject to any disclaimer, the term of this patent is extended or adjusted under 35 U.S.C. 154(b) by 406 days.

(21) Appl. No.: 17/428,903

(22) PCT Filed: Feb. 25, 2020

(86) PCT No.: PCT/EP2020/054859
§ 371 (c)(1),
(2) Date: Aug. 5, 2021

(87) PCT Pub. No.: WO2020/173916
PCT Pub. Date: Sep. 3, 2020

(65) Prior Publication Data
US 2022/0130507 A1 Apr. 28, 2022

(30) Foreign Application Priority Data

Feb. 25, 2019 (EP) ..................................... 19461515

(51) Int. Cl.
*G16H 20/30* (2018.01)
*A61N 1/36* (2006.01)
(Continued)

(52) U.S. Cl.
CPC ......... *G16H 20/30* (2018.01); *A61N 1/36025* (2013.01); *A61N 1/36034* (2017.08);
(Continued)

(58) Field of Classification Search
CPC .... G16H 20/30; G16H 40/63; A61N 1/36025; A61N 1/36034; G09B 19/04
See application file for complete search history.

(56) References Cited

U.S. PATENT DOCUMENTS

| | | |
|---|---|---|
| 2008/0146959 A1 | 6/2008 | Sheffield et al. |
| 2014/0172041 A1 | 6/2014 | Draghici et al. |
| | (Continued) | |

FOREIGN PATENT DOCUMENTS

| | | |
|---|---|---|
| CN | 105 664 357 A | 6/2016 |
| EP | 3 106 202 A1 | 12/2016 |
| | (Continued) | |

OTHER PUBLICATIONS

Jimenez-Molina A, Retamal C, Lira H. Using Psychophysiological Sensors to Assess Mental Workload During Web Browsing. Sensors (Basel). Feb. 3, 2018;18(2):458. doi: 10.3390/s18020458. PMID: 29401688; PMCID: PMC5855035. (Year: 2018).*

(Continued)

*Primary Examiner* — Tammie K Marlen
*Assistant Examiner* — Maria Catherine Anthony
(74) *Attorney, Agent, or Firm* — Leydig, Voit & Mayer, Ltd.

(57) ABSTRACT

The disclosure relates to a brain stimulation system (102), comprising: a) a computer program product, e.g. a data carrier, preferably a non-transitory data carrier, or a data stream, comprising program code (P1, P1*a*) which, when loaded and executed on an electronic control unit (108), provides an operation control system, orb) an electronic control unit (108) with a program code (P1, P1*a*) loaded on (Continued)

Figure 1:
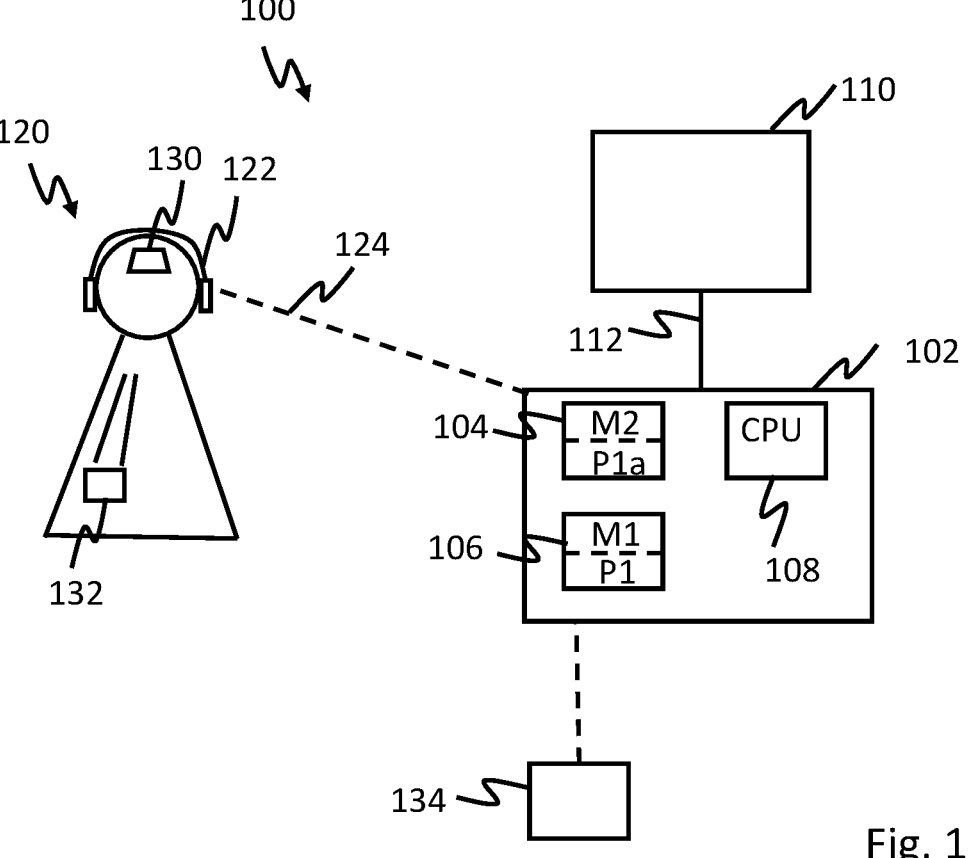

the electronic control unit (108), wherein the program code (P1, P1a), when executed on the electronic control unit (108), provides an operation control system (200), wherein the operation control system (200) is configured to control a brain training and/or stimulation session for a brain, and wherein the operation control system (200) comprises a plurality of control system functionalities, the control system functionalities comprising: —a stimulation functionality (202) which is configured to cause the electronic control unit (108) to issue a stimulation command to an electrical brain stimulation device (122) to cause the electrical brain stimulation device (122) to perform an electrical brain stimulation procedure; and—a presentation functionality (204) which is configured to cause the electronic control unit (108) to issue a presentation command in order to present a task to be performed by a user (120) on a user interface (110), wherein preferably the stimulation functionality (202) and the presentation functionality (204) are linked (254 to 262) or linkable to one another.

30 Claims, 5 Drawing Sheets

(51) Int. Cl.
G09B 7/00 (2006.01)
G09B 19/04 (2006.01)
G16H 40/63 (2018.01)
(52) U.S. Cl.
CPC ............. G09B 19/04 (2013.01); G16H 40/63 (2018.01); G09B 7/00 (2013.01)

(56) References Cited

U.S. PATENT DOCUMENTS

| 2017/0361096 | A1* | 12/2017 | Wingeier | ............. | A61B 5/4836 |
| 2022/0351825 | A1 | 11/2022 | Malej et al. | | |

FOREIGN PATENT DOCUMENTS

| WO | WO 2007138598 | A3 | 12/2007 | | |
| WO | WO 2007/138598 | A2 | 12/2017 | | |
| WO | WO-2018071426 | A1 * | 4/2018 | ........... | A61B 5/0075 |

OTHER PUBLICATIONS

Pollok et al. (2015) "The effect of transcranial alternating current stimulation (tACS) at alpha and beta frequency on motor learning", Behav. Brain Res. 293: 234-240; doi:10.1016/j.bbr.2015.07.049.
International Search Report and Written Opinion mailed May 19, 2020 in PCT/EP2020/054859.
Written Opinion mailed Jan. 29, 2021 in PCT/EP2020/054859.
International Preliminary Report on Patentability mailed Jun. 8, 2021 in PCT/EP2020/054859.
Pawel Soluch (2018) "Neuro Device" Chivas Venture 2018; Retrieved from the Internet: URL:https://www.chivas.com/pl-pl/the-venture/alumni/2018/pl-pawel-soluch.
Anonymous: "NeuroDevice Voic" Jun. 2018, Retrieved from the Internet: URL:http://www.neurodevice.pl/wp-content/uploads/2018/06/Voic brochure-1.pdf.
Shah-Basak et al. (Apr. 21, 2015) "Individualized treatment with transcranial direct current stimulation in patients with chronic non-fluent aphasia due to stroke", Frontiers in Human Neuroscience, 9(21): 1-12; DOI: 10.3389/fnhum.2015.00201 abstract.
Holland et al. (2012) "Can tDCS enhance treatment of aphasia after stroke?", Aphasiology, 26(9): 1169-1191; DOI: 10.1080/02687038.2011.616925.
Nikolaev et al. (2001) "Correlation of brain rhythms between frontal and left temporal (Wernicke's) cortical areas during verbal thinking", Neuroscience Letters, 298: 107-110.
Nowak et al. (Apr. 26, 2017) "Driving Human Motor Cortical Oscillations Leads to Behaviorally Relevant Changes in Local $GABA_A$ Inhibition: A tACS-TMS Study", The Journal of Neuroscience, 37(17): 4481-4492; https://doi.org/10.1523/JNEUROSCI.0098-17.2017.
Gaona et al. (Feb. 9, 2011) "Nonuniform High-Gamma (60-500 Hz) Power Changes Dissociate Cognitive Task and Anatomy in Human Cortex", The Journal of Neuroscience, 31(6): 2091-2100; DOI:10.1523/JNEUROSCI.4722-10.2011.
Bates et al. (2015) "Fitting Linear Mixed-Effects Models Using lme4," Journal of Statistical Software 67(1), 1-48. https://doi.org/10.18637/jss.v067.i01.
Borenstein (1997) "Hypothesis testing and effect size estimation in clinical trials," Annals of Allergy, Asthma & Immunology, 78, 1, pp. 5-12, 15-16.
Bucur et al. (Jul. 2019) "Are transcranial brain stimulation effects long-lasting in post-stroke aphasia? A comparative systematic review and meta-analysis on naming performance," Neuroscience and Biobehavioral Reviews 102, 264-289.
Buzsáki et al. (2004) "Neuronal Oscillations in Cortical Networks," Science 304, 1927-1929.
Fregni et al. (Apr. 2021) "Evidence-Based Guidelines and Secondary Meta-Analysis for the Use of Transcranial Direct Current Stimulation in Neurological and Psychiatric Disorders," International Journal of Neuropsychopharmacology 24(4): 256-313.
Fridriksson et al. (Jan. 2019) "Transcranial direct current stimulation to treat aphasia: Longitudinal analysis of a randomized controlled trial," Brain Stimulation 12, 190-191.
Lakens (2013) "Calculating and reporting effect sizes to facilitate cumulative science: a practical primer for t-tests and ANOVAs," Front. in Psychol. 4, 863, 12 pp. doi: 10.3389/fpsyg.2013.00863.
Meinzer et al. (2016) "Electrical stimulation of the motor cortex enhances treatment outcome in post-stroke aphasia," Brain 139, 4, 1152-1163.
Nakagawa (2004) "A farewell to Bonferroni: the problems of low statistical power and publication bias," Behavioral Ecology 15, 6, 1044-1045.
Sullivan et al. (2012) "Using Effect Size-or Why the P Value Is Not Enough," J Grad Med Educ 4(3): 279-282.
Zuo et al. (2010) "The Oscillating Brain: Complex and Reliable," Neuroimage 49(2): 1432-1445.
European Search Report issued in EP22183618.2 on Oct. 24, 2022.
Office Action for EP Patent Application No. 22183618.2 issued Jan. 22, 2025, 7 pp.

* cited by examiner

BRAIN STIMULATION SYSTEM, DEVICE, ARRANGEMENT AND CORRESPONDING METHOD FOR TREATING APHASIA

CROSS-REFERENCE TO RELATED APPLICATIONS

This application is a U.S. National Stage Application under 35 U.S.C. § 371 of International Application No. PCT/EP2020/054859, filed Feb. 25, 2020, which claims the benefit of and priority to European Patent Application No. 19461515.9, filed Feb. 25, 2019. Each of these applications is hereby incorporated by reference in its entirety.

The disclosure relates to a brain stimulation system, especially to a brain stimulation system that may be used for treating aphasia. Furthermore, a corresponding device, arrangement and method will be described.

Methods and devices are known for treatment of aphasia using constant current, e.g. tDCS (transcranial Direct Current Stimulation), see for instance R. Holland and J. Crinion, "Can tDCS enhance treatment of aphasia after stroke?" *Aphasiology*, vol. 26, no. 9, pp. 1169 to 1191, 2012. However, usability of known devices and methods for treating aphasia may have potential for improvement as may have electrical brain stimulation systems, methods and devices in general.

It is an object of the disclosure to provide an improved brain stimulation system, especially by providing functionalities that improve usability of the brain stimulation system, preferably in connection with or for the treatment of aphasia. Furthermore, a corresponding device, arrangement and method shall be given.

This object may be achieved by the brain stimulation system according to claim 1 and by the device, arrangement and corresponding method according to the independent claims. Further advantageous embodiments are given in the dependent claims.

In one aspect the brain stimulation system comprises:

a) a computer program product, e.g. a data carrier (such as a memory stick, CD (compact disc), magnetically storing hard disk (HD), SSD (Solid State Device)), preferably a non-transitory data carrier, or a data stream (on wire or wirelessly transmitted, e.g. digital and/or analog signals), comprising program code which, when loaded and executed on an electronic control unit (e.g. comprised by a notebook, a PC, a tablet, a mobile phone or a smartphone), provides an operation control system, or b) an electronic control unit with a program code loaded on the electronic control unit, wherein the program code, when executed on the electronic control unit, provides an operation control system, wherein, for a) and/or b), the operation control system is configured to control a brain training and/or stimulation session for a brain, and wherein the operation control system comprises at least one or a plurality of control system functionalities, the control system functionalities comprising:

a stimulation functionality which is configured to cause the electronic control unit to issue a stimulation command to an electrical brain stimulation device to cause the electrical brain stimulation device to perform an electrical brain stimulation procedure; and/or a presentation functionality which is configured to cause the electronic control unit to issue a presentation command in order to present a task to be performed by a user on a user interface.

Preferably, the stimulation functionality and the presentation functionality may be linked or may be linkable to one another. The electrical brain stimulation procedure may be a transcranial stimulation procedure.

The stimulation functionality and the presentation functionality may especially be timely linked or synchronized, e.g. such that the brain stimulation procedure is performed while tasks are presented to and/or performed by the user. The brain stimulation procedure may be performed for all tasks presented during a stimulation session or only for selected or special tasks, for instance tasks that are more difficult than other tasks presented in the same session. By means of electrical brain stimulation the brain stimulation system may positively influence the activity of neurons in the stimulated part of the brain. Expediently, the stimulated part(s) or region(s) of the brain is active when performing the task and/or used to solve the tasks that are presented by the presentation functionality. During a brain training combined with stimulation session, neuronal network strengthening may efficiently support therapy processes and the user may improve the brain function, e.g. language processing and/or speech generation ability in a comparably short time due to this double influence to the neurons, e.g. by electrical stimulation and the natural brain activations involved in performing the task. The user's performance may be improved due to the additional electrical brain stimulation while presenting and/or performing the task. The linking of brain stimulation to the tasks which are performed may have a positive influence on, for example: the training effect for the brain, i.e. neuroplasticity, and/or the user's motivation to do several training sessions. The proposed system may be particularly suitable for users suffering from aphasia, e.g. after having suffered a stroke.

Additionally or alternatively, the stimulation functionality and the presentation functionality may especially be linkable or linked, e.g. time-synchronized, such that for instance a preparation stimulation is performed before the first task of the current session is performed and/or presented. The preparation stimulation may be provided as an alternative or in addition to a task stimulation, which is performed during presentation and/or performance of the task. The plasticity of relevant brain areas may be increased by the preparation stimulation. Thus, the training efficiency may be improved even more.

In other words, the term "linked" may mean that the scheduling of the stimulation functionality and of the presentation functionality is coordinated with regard to each other, for instance by the operation control system. Scheduling refers for instance to at least one of: the time of the beginning of the stimulation procedure, the time of the beginning of the presentation of tasks, the time of terminating the stimulation procedure, and the time of terminating the presentation of tasks.

The term "linked" may further mean that the kind of stimulation and/or the intensity of stimulation, e.g. amplitude, duration, etc., may depend on the kind of task that has to be performed.

Thus, there is preferably an electrical brain stimulation functionality of specific brain areas used in combination, for instance also at the same time, with a presentation functionality that excites or activates the same brain areas of the user through physiological brain activity processes, in particular without external electrical stimulation. The combination of these two functionalities allows synergistic effects between both functionalities that are not possible if only one of the procedures is used or if there is no linkage between both functionalities.

The electrical brain stimulation procedure may be performed transcranially on the user, e.g. by using at least one electrode, two electrodes or a plurality of electrodes that are connected and/or fixed to the head of the user of the brain stimulation system. The user may be a patient that suffers from aphasia. Alternatively the user may be a healthy person that intends to improve his or her language processing and/or production skills.

The stimulation functionality is described in more detail below see section A. The presentation functionality is described in more detail in section B below. Stimulation data may be used that is contained in the stimulation command or that is stored in a memory of the brain stimulation system. Details of this stimulation data are also mentioned below.

The stimulation functionality may comprise a preparation stimulation functionality for a preparation stimulation and/or a task stimulation functionality for a task stimulation. The preparation stimulation may be configured to be performed, preferably completed, before the task, preferably the first task, is presented to the user. The task stimulation may be configured to be synchronized with the presentation of the task, preferably performed during the presentation of the task to the user and/or during the performance of the task by the user.

The preparation stimulation may be used to increase brain plasticity. This may facilitate learning processes during the presentation and performance of tasks. Preferably, the preparation functionality is used or is available to be used only once during the brain stimulation and/or training session, e.g. initially before the first task is presented to the user or the associated command is issued.

The type of stimulation in the stimulation procedure, e.g. in the preparation stimulation and/or the task stimulation, may be specified in the stimulation command to be transcranial electrical stimulation in constant current mode (transcranial direct current stimulation (tDCS)) or in varying current mode (e.g. transcranial alternating current stimulation (tACS), transcranial random noise stimulation (tRNS), pulses of current) or a sequence thereof.

The duration of the preparation stimulation may be greater than or equal to one of the following values: 5, 6, 7, 8, 9, 10, 11, 12, 13, 14, 15, 16, 17, 18, 19, 20 minutes. Alternatively or additionally, the duration of the preparation stimulation may be less than or equal to one of the following values: 90, 80, 70, 60, 55, 50, 45, 40, 35, 30, 29, 28, 27, 26, 25, 24, 23, 22, 21, 20 minutes. All combinations between lower limits and upper limits are possible, for instance 10 to 25 minutes. Thus, ranges may be formed by combining values from the lower limits and from the upper limits.

The preparation stimulation may be a constant current stimulation. The amplitude of constant or direct current (DC) may be in the range of 0.1 mA to 10 mA or 0.1 to 5 mA, preferably 2 mA. Alternatively or additionally the amplitude of the direct current may be greater than or equal to one of the following values: 0.1, 0.2, 0.3, 0.4, 0.5, 0.6, 0.7, 0.8, 0.9, 1, 2, 3, 4, 5 mA. Alternatively or additionally, the amplitude of the direct current may be less than or equal to one of the following values: 10, 9, 8, 7, 6, 5 mA. All combinations between lower limits and upper limits are possible, for instance 1 to 7 mA. Thus, ranges may be formed by combining values from the lower limits and from the upper limits.

Alternatively the preparation stimulation may be a varying current stimulation. For example tRNS, may be particularly suitable for a preparation stimulation in the varying current mode.

The task stimulation may preferably be a varying current stimulation. "Varying" may mean that the current is non-constant, preferably sinusoidal. The frequency of the stimulation, e.g. the frequency of stimulation in the specific brain area and/or the frequency of the varying current, may be in the range of 13 Hz (hertz) to 24 Hz, especially 17 Hz. Beta oscillation, e.g. in the range of 12.5 Hz to 30 Hz, may be preferred for the treatment of aphasia. Alternatively or additionally, the frequency may be greater than or equal to one of the following values: 12, 13, 14, 15, 16, 17, 18, 19 Hz. Alternatively or additionally, the frequency may be less than or equal to one of the following values: 25, 24, 23, 22, 21, 20, 19 Hz (Hertz). All combinations between lower limits and upper limits are possible, for instance 12 to 22 Hz. Thus, ranges may be formed by combining values from the lower limits and from the upper limits.

It has been shown, that beta frequency tACS (20 Hz) are most efficient in boosting neuroplastic effects in motor cortex (motor learning)—see Pollok et al., "The effect of transcranial alternating current stimulation (tACS) at alpha and beta frequency on motor learning", Behavioural Brain Research 293 (2015) 234-240, which is incorporated by reference herewith. In Wernicke's area, similarly to motor cortex, there are also present oscillations of beta frequency. Specifically, it has been shown, that 17 Hz frequency is one of the most pronounced in Wernicke's activity (see Nikolaev et al., "Correlation of brain rhythms between frontal and left temporal (Wernicke's) cortical areas during verbal thinking", Neuroscience Letters 298 (2001) 107-110, which is incorporated by reference herewith). Without to be bound by theory, based on that we hypothesized that 17 Hz stimulation may be particularly efficient for aphasia therapy.

However, additionally or alternatively, other frequency ranges may also be relevant, for instance alpha oscillation, as indicated in scientific papers, e.g. in the frequency range of 7.5 Hz to 12.5 Hz. The frequency may be greater than or equal to one of the following values: 7, 8, 9 Hz. The frequency may be less than or equal to one of the following values: 13, 12, 11, 10, 9 Hz. All combinations between lower limits and upper limits are possible, for instance 8 to 11 Hz.

Other frequencies may be also relevant, for instance delta (1-4 Hz), theta (4-8 Hz), low gamma (30-70 Hz) and high gamma (70-150 Hz). In particular, a frequency of 75 Hz may be used or a frequency within the range of 70 Hz to 80 Hz or of 60 Hz to 100 Hz or of 60 Hz to 250 Hz.

The following alternatives may be used for the frequency of the stimulation, e.g. preparation stimulation and/or task stimulation:

alternative b), the frequency of varying current may be or is in the range of 70 Hz (hertz) to 80 Hz, e.g. 75 Hz, in the alternative b), the frequency of varying current is preferably greater than or equal to one of the following values: 69, 70, 71, 72, 73, 74, 75, 76, 77, 78, 79 Hz, in the alternative b), the frequency of varying current is preferably less than or equal to one of the following values: 80, 79, 78, 77, 76, 75, 74, 73, 72 or 71 Hz, alternative c), the frequency of varying current may be or is in the range of 60 Hz (hertz) to 100 Hz, e.g. 75 Hz or 80 Hz, in the alternative c), the frequency of varying current is preferably greater than or equal to one of the following values: 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 88 or 99 Hz, in the alternative c), the frequency of varying current is preferably less than or equal to one of the following values: 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62 or 61 Hz, alternative d), the frequency of varying current may be or is in the range of 60 Hz (hertz) to 250 Hz, e.g. 60, 70, 80, 90, 100, 110, 120, 130, 140, 150, 160, 170, 180, 190, 200, 210, 220, 230, 240 or 250 Hz, in the alternative d), the frequency of varying current is preferably greater than or equal to one of the following values: 60, 70, 80, 90, 100, 110, 120, 130, 140, 150, 160, 170, 180, 190, 200, 210, 220, 230, 240 Hz, in the alternative d), the frequency of varying current is preferably less than or equal to one of the following values: 250, 240, 230, 220, 210, 200, 190, 180, 170, 160, 150, 140, 130, 120, 110, 100, 90, 80 or 70 Hz, alternative e), the frequency of varying current may be or is in the range of 30 Hz (hertz) to 70 Hz, e.g. 30, 35, 40, 45, 50, 55, 60, 65 or 70 Hz, in the alternative e), the frequency of varying current is preferably greater than or equal to one of the following values: 30, 35, 40, 45, 50, 55, 60 or 65 Hz, in the alternative e), the frequency of varying current is preferably less than or equal to one of the following values: 70, 65, 60, 55, 50, 45, 40 or 35 Hz, alternative f), the frequency of varying current may be or is in the range of 70 Hz (hertz) to 150 Hz, e.g. 70, 75, 80, 85, 90, 95, 100, 105, 110, 115, 120, 125, 130, 135, 140, 145 or 150 Hz, in the alternative f), the frequency of varying current is preferably greater than or equal to one of the following values: 70, 75, 80, 85, 90, 100, 105, 110, 115, 120, 125, 130, 135, 140 or 145 Hz, in the alternative f), the frequency of varying current is preferably less than or equal to one of the following values: 150, 145, 140, 135, 130, 125, 120, 115, 110, 105, 100, 95, 90, 85, 80 or 75 Hz.

In studies on motor cortex it has been shown that for instance by 75 Hz transcranial alternating current stimulation a decrease of the $GABA_A$ (gamma-aminobutyric acid receptor type A) inhibition is more pronounced comparing to other methods, see for instance Nowak et al., "Driving Human Motor Cortical Oscillations Leads to Behaviorally Relevant Changes in Local $GABA_A$ Inhibition: A tACS-TMS Study", Journal of Neuroscience, 2017, https://doi.org/10.1523/JNEUROSCI.0098-17.2017, which is incorporated by reference herewith. "TMS" stands for transcranial magnetic stimulation. Without to be bound by theory, a decrease of the $GABA_A$ inhibition may promote motor cortex activation of the person whose brain is stimulated, i.e. rendering the stimulated area more prone to neuroplastic processes. Again without to be bound to theory, the link between movement and aphasia may be that movement of lips and/or tongue and/or movement of the jaw and/or voluntary breathing movements are necessary to speak and motor cortex, especially supplementary motor area, plays important role in the process of speaking. Furthermore, similar effects related to $GABA_A$ inhibition may occur in other areas of the brain, e.g. Wernicke's and/or Broca's areas.

Without to be bound by theory, it is hypothesized, that $GABA_A$ inhibition may be particularly decreased, if the stimulation frequency reflects the natural oscillation occurring in the stimulated brain area. The presence of oscillations within the range of 60 Hz to 100 Hz in the area of Wernicke and in the range of 60 Hz to 250 Hz in the area of Broca was proved using ECoG, see for instance Gaona et al., "Non-uniform high-gamma (60-500 Hz) power changes dissociate cognitive task and anatomy in human cortex." 2011, J Neurosci. February 9; 31(6):2091-100. doi: 10.1523/JNEU- ROSCI.4722-10.2011), which is incorporated by reference herewith. "ECoG" stands for electrocorticographic signals.

The amplitude of the varying current stimulation may be in the range of 0.1 mA to 10 mA or 0.1 to 5 mA, preferably 2 mA. Alternatively or additionally, the amplitude may be greater than or equal to one of the following values: 0.1, 0.2, 0.3, 0.4, 0.5, 0.6, 0.7, 0.8, 0.9, 1, 2, 3, 4, 5 mA (milliampere). Alternatively or additionally, the amplitude may be less than or equal to one of the following values: 10, 9, 8, 7, 6, 5 mA. All combinations between lower limits and upper limits are possible, for instance 1 to 7 mA. Thus, ranges may be formed by combining values from the lower limits and from the upper limits.

The operation control system may be configured such that during the brain training and/or stimulation session at least one stimulation command for varying current mode is issued. This stimulation command may be synchronized with the presentation of a task on the user interface. The stimulation command may be a command for a stimulation in the alternating current mode (tACS). The current in alternating current mode may have the same or a similar frequency that is also present in the natural oscillation of neurons in the relevant brain areas—preferably while performing a task, e.g. brain areas that are relevant for language processing and/or production. It is believed that using the same frequencies may interact with natural brain waves occurring while activating the specific brain area, thus facilitating activation of the brain area. If the same frequencies are used there may be a kind of resonance effect, e.g. it may be possible to amplify the natural oscillation of neurons.

The operation control system may be configured such that during the brain training and/or stimulation session a plurality of presentation commands is issued to present different tasks on the user interface. Preparation stimulation may be performed, preferably before the first presentation command is issued. Only one preparation stimulation may be performed, preferably before the first presentation command is issued. It may also be considered to perform a plurality of preparation stimulations, e.g. with different parameter and/or consecutively. Different kinds of tasks may be used to present an interesting series of tasks and to prevent that the user gets tired or is bored. Tasks of different levels of difficulty may be used as well alternatively and/or additionally to different kinds of tasks. The stimulation may be adapted to the kind of task and/or to the level of difficulty of the specific task.

The presentation functionality may be configured to select the task to be presented on the user interface from a plurality of, preferably predefined, tasks of different levels of difficulty. The level of difficulty of the task to be presented may be selected by the presentation functionality based on presentation data provided to, e.g. by a practitioner, such as a physician, or calculated by the operation control system. The presentation data may be adjusted depending on and/or contain information on performance data of one or more previous tasks in the current session and/or one, more or all tasks in a former session, especially on performance data of the last session of the same user.

Further aspects of the disclosure relate to further functionalities, e.g. to:

a performance assessment functionality (see section E below for more details), a stimulation adjustment functionality (see section I below for more details), a user feedback functionality (see section G below for more details), a user condition monitoring functionality (see section D below for more details), a session number tracking functionality (see section H below for more details), and/or a telemetry or transmission functionality (see section F below for more details).

The respective functionality may be subject to a dependent claim. However, it should be appreciated that each of the functionalities may be present alternatively or additionally to the presentation and/or the stimulation functionality discussed further above.

For example, performance assessment, e.g. comprising an evaluation of whether and how good the user performs the task, may be the basis for an adjustment of parameters that are used for the stimulation procedure, e.g. the stimulation command, either during the current session or a subsequent session and/or for the presentation data either during the current session or a subsequent session. Some of these parameters are explained in more detail below. There may be for instance the following strategy: The intensity of the electrical brain stimulation may be decreased step by step when the language processing and/or performance abilities of the user improve. The task stimulation procedure and/or the preparation stimulation procedure may be skipped. The aim is to have no electrical brain stimulation at the end of a series of sessions, e.g. close to the end of a successful therapy of aphasia. This means that the user is able to speak and/or write on its own abilities then. During the tasks, the electrical brain stimulation may be used only selectively, for instance in order to enable the user to solve more difficult tasks by support of the electrical brain stimulation, especially if this type of task is presented for the first time. For example, simpler tasks or tasks that the user is or has been already able to solve on his or her own reliably may be presented without electrical brain stimulation. Alternatively, electrical brain stimulation is possible for all tasks or for no tasks during the task presentation.

However, other strategies for the adjustment of stimulation parameters may be used as well. The adjustment may depend on performance assessment and/or on other factors.

The functionalities disclosed above improve usability and flexibility of the system considerably. User feedback may be very important for user motivation which influences the emotional state of the user and especially the state of the brain in a positive sense. Furthermore, user condition monitoring may be used to monitor the cognitive load and emotional state of the user in order to ensure the best results for improvement of language abilities and prevent cognitive overloads, thus facilitate maintaining attention. Beneficial attention may be maintained longer if there are intermediate phases, e.g. of a fixed or adjustable duration, with no presentation of tasks and/or with no electrical stimulation procedures, preferably between two succeeding presentation commands. Whether an intermediate phase is applied between two succeeding tasks may be decided dependent on user condition data supplied to the operation control system. The session number tracking functionality and/or the telemetry or transmission functionality may enhance the usability further. Each functionality is described below in more detail.

Stimulation data that may be relevant for and/or contained in the stimulation command may comprise one, an arbitrarily selected plurality of, or all of the following stimulation parameters:

amplitude and/or offset, e.g. different from 0 microampere or 0 mA, of the current signal for the varying current stimulation procedure; The offset may refer to the mean value of the signal, especially if the signal is sinusoidal, trapezoid or has a rectangular form. Alternatively, the Offset may refer to the minimum value of the signal.

frequency, range of frequencies, phase and/or range of phases, and/or offset of the current signal for the alternating current stimulation procedure;

presence or absence of an electrical brain preparation stimulation procedure performed, for instance in the constant current stimulation mode in the same stimulation session but before presentation of the task and/or before a main electrical brain stimulation, for instance in the varying current stimulation procedure;

magnitude of the current applied in the constant current stimulation procedure;

duration of the electrical brain stimulation procedure, e.g. the preparation stimulation;

start of the electrical brain stimulation procedure, e.g. the task stimulation, relative to the onset of the presentation of the task, e.g. before, together with and/or after the task presentation; and/or duration of the electrical brain stimulation procedure, e.g. the task stimulation, relative to a typical duration required for performing the task or by using an absolute value.

Thus, the stimulation data enables easy control of the brain stimulation system. The frequency and/or the amplitude of the varying current may be specified in the stimulation data using the values that are listed in the description. The amplitude of the constant current may also be specified in the stimulation data using the values that are listed in the description. The duration of the stimulation may be linked to the duration for the performance of a single task, e.g. the actual duration or a predetermined, preferably typical, duration.

The stimulation data may preferably refer to a varying current stimulation. "Varying" may mean that the current is non-constant. The frequency of the stimulation that is specified within the stimulation data, e.g. the frequency of stimulation in the specific brain area and/or the frequency of the varying current, may be in the range of 13 to 24 hertz (Hz, i.e. cycles per second) and may especially have the value of 17 Hz. Beta oscillation, e.g. in the range of 12.5 Hz to 30 Hz, may be preferred for the treatment of aphasia. Alternatively or additionally, the frequency that is specified within the stimulation data may be greater than or equal to one of the following values: 12, 13, 14, 15, 16, 17, 18, 19 Hz. Alternatively or additionally, the frequency that is specified within the stimulation data may be less than or equal to one of the following values: 25, 24, 23, 22, 21, 20, 19 Hz. All combinations between lower limits and upper limits are possible, for instance 12 to 22 Hz. Thus, ranges may be formed by combining one selected value from the lower limit and one selected value from the upper limit.

The following alternatives may be used for the frequency specified in the stimulation data, e.g. in preparation stimulation data and/or in task stimulation data:

alternative b), the frequency of varying current may be or is in the range of 70 Hz (hertz) to 80 Hz, e.g. 75 Hz, in the alternative b), the frequency of varying current is preferably greater than or equal to one of the following values: 69, 70, 71, 72, 73, 74, 75, 76, 77, 78, 79 Hz, in the alternative b), the frequency of varying current is preferably less than or equal to one of the following values: 80, 79, 78, 77, 76, 75, 74, 73, 72 or 71 Hz, alternative c), the frequency of varying current may be or is in the range of 60 Hz (hertz) to 100 Hz, e.g. 75 Hz or 80 Hz, in the alternative c), the frequency of varying current is preferably greater than or equal to one of the following values: 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 88 or 99 Hz, in the alternative c), the frequency of varying current is preferably less than or equal to one of the following values: 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62 or 61 Hz, alternative d), the frequency of varying current may be or is in the range of 60 Hz (hertz) to 250 Hz, e.g. 60, 70, 80, 90, 100, 110, 120, 130, 140, 150, 160, 170, 180, 190, 200, 210, 220, 230, 240 or 250 Hz, in the alternative d), the frequency of varying current is preferably greater than or equal to one of the following values: 60, 70, 80, 90, 100, 110, 120, 130, 140, 150, 160, 170, 180, 190, 200, 210, 220, 230, 240 Hz, in the alternative d), the frequency of varying current is preferably less than or equal to one of the following values: 250, 240, 230, 220, 210, 200, 190, 180, 170, 160, 150, 140, 130, 120, 110, 100, 90, 80 or 70 Hz, alternative e), the frequency of varying current may be or is in the range of 30 Hz (hertz) to 70 Hz, e.g. 30, 35, 40, 45, 50, 55, 60, 65 or 70 Hz, in the alternative e), the frequency of varying current is preferably greater than or equal to one of the following values: 30, 35, 40, 45, 50, 55, 60 or 65 Hz, in the alternative e), the frequency of varying current is preferably less than or equal to one of the following values: 70, 65, 60, 55, 50, 45, 40 or 35 Hz, alternative f), the frequency of varying current may be or is in the range of 70 Hz (hertz) to 150 Hz, e.g. 70, 75, 80, 85, 90, 95, 100, 105, 110, 115, 120, 125, 130, 135, 140, 145 or 150 Hz, in the alternative f), the frequency of varying current is preferably greater than or equal to one of the following values: 70, 75, 80, 85, 90, 95, 100, 105, 110, 115, 120, 125, 130, 135, 140 or 145 Hz, in the alternative f), the frequency of varying current is preferably less than or equal to one of the following values: 150, 145, 140, 135, 130, 125, 120, 115, 110, 105, 100, 95, 90, 85, 80 or 75 Hz.

Other ranges of frequency may be used as well, especially ranges that are mentioned in this description.

The amplitude of the varying current that is specified within the stimulation data may be in the range of 0.1 mA to 10 mA or 0.1 to 5 mA, preferably 2 mA. Alternatively or additionally, the amplitude that is specified within the stimulation data may be greater than or equal to one of the following values: 0.1, 0.2, 0.3, 0.4, 0.5, 0.6, 0.7, 0.8, 0.9, 1, 2, 3, 4, 5 mA (milliampere). Alternatively or additionally, the amplitude that is specified within the stimulation data may be less than or equal to one of the following values: 10, 9, 8, 7, 6, 5 mA. All combinations between lower limits and upper limits are possible, for instance 1 mA to 7 mA. Thus, ranges may be formed by combining one selected value from the lower limit and one selected value from the upper limit.

The amplitude of the constant/direct current that is specified within the stimulation data may be in the range of 0.1 milliampere (mA) to 10 mA or 0.1 mA to 5 mA, preferably 2 mA. Alternatively or additionally, the amplitude of the direct current that is specified within the stimulation data may be greater than or equal to one of the following values: 0.05, 0.1, 0.2, 0.3, 0.4, 0.5, 0.6, 0.7, 0.8, 0.9, 1, 2, 3, 4, 5 mA. Alternatively or additionally, the amplitude of the direct current that is specified within the stimulation data may be less than or equal to one of the following values: 11, 10, 9, 8, 7, 6, 5 mA. All combinations between lower limits and upper limits are possible, for instance 1 to 7 mA. Thus, ranges may be formed by combining one selected value from the lower limit and one selected value from the upper limit.

There may be a session operation protocol interface functionality (see section J below) that may change the stimulation data as well. An authentication procedure may be used to make sure that sensible data is changed only by the authorized persons, e.g. a specialized practitioner or by a general practitioner. The practitioner may have a medical degree. The practitioner may be a physician or a therapist The respective task may be e.g. a task that is related to language comprehension and/or language production. This may be particularly suitable for treatment of aphasia. Language may be presented in the task, e.g. by speech or in writing. The user may process what is presented by comprehension. Then the user may produce a language related output, e.g. in speech or writing, in order to perform the task. Types of useful tasks are for instance: repetitions, answering of questions, associating a semantically related word (use-generation task) to a word or to a picture that is presented to the user, etc. Writing tasks may be easier to evaluate automatically via the performance assessment functionality compared to spoken words. If task performance requires speaking, automatic speech recognition may be used to assess the performance, nevertheless. However, as compared to automatic handwriting recognition or to data put in using a keyboard or an alpha-numerical input device, this may still require more computational resources. The focus on language-related tasks may be an important component for a brain stimulation system that is appropriate for the treatment of aphasia.

The task may comprise the presentation of words or sentences, pictures, pictograms, etc. To solve the task the user may need to comprehend presented words or sentences, to recognize the content of the picture or pictogram and/or to actively produce language related output in speech or writing. Different kinds of tasks may comprise repetitions, answering of questions, descriptions of the content of pictures or supply of semantically related words, e.g. use-generation task. As noted already above, writing tasks may be easier to be evaluated via the performance assessment functionality than tasks that have to be answered verbally.

The brain stimulation system may be an aphasia treatment system or may be part of an aphasia treatment system. Aphasia is an inability to comprehend or formulate language because of damage to specific brain regions. There may be the following communication modalities that have deficits: auditory comprehension, verbal expression, reading and/or writing, functional communication (functional tasks, social interaction, self-expression), etc. Millions of people suffer from aphasia worldwide.

Thus there is a strong need for an aphasia treatment system that is simple and that has excellent usability.

The operation control system may comprise a control functionality that is part of the link or that forms the link between stimulation functionality and presentation functionality. Thus the control functionality may be a core functionality of the proposed brain stimulation system and especially of the operation control system. Further details of the control functionality are described below in section C.

The disclosure also relates to a brain stimulation device. The brain stimulation device may be configured to stimulate a brain, preferably a human brain, electrically and transcranially. The brain stimulation device may be configured to be mounted on a head of a user for a brain training and/or stimulation session. The brain stimulation device may be configured to be operated to stimulate the brain via varying, especially alternating, current stimulation (e.g. tACS, tRNS, or pulsed operation) in a varying current mode of operation. Constant current stimulation (e.g. tDCS) may be used in a constant current mode of operation in a stimulation procedure. The brain stimulation device may be the brain stimulation device that is used in the brain stimulation system or one of its embodiments or variations as disclosed above or below. Thus, features, advantages and technical effects that are valid for the brain stimulation system and its embodiments may also be valid for the brain stimulation device and vice versa.

The brain stimulation device may have at least one, two, three, four or all of the following features:

a) in the alternating current mode of operation or in the varying current mode of operation, a frequency or range of frequencies of the alternating current used to stimulate the brain may be adjusted or may be adjustable to a frequency which is characteristic for the brain rhythm, that occurs while performing a task, especially a treatment task, in an area of the brain which is to be stimulated via alternating current, and/or b) the brain stimulation device may further comprise a device controller, wherein the device controller is configured to select the mode of operation—varying current mode of operation or constant current mode of operation—for the stimulation procedure and/or to set one or more stimulation parameters such that the respective stimulation procedure is performed according to the stimulation parameters, and/or c) the brain stimulation device may have a, preferably wireless, interface for operative connection of the device to an electronic control unit, and/or d) wherein, during operation of the brain stimulation device, the device may be configured to stimulate, electrically and transcranially, a specific brain area or areas, related to treated function, e.g. comprising Wernicke's area and/or Broca's area for speech therapy, wherein, preferably, the respective one area or more areas can be stimulated via constant current mode and/or varying current mode.

The disclosure further relates to a brain stimulation arrangement that comprises the brain stimulation system or its embodiments and/or a brain stimulation device or its embodiments, and a user condition monitor device. The device may be configured to monitor one or more physiological parameters of the user, preferably physiological parameters, such as parameters indicative for the cognitive workload of the user. Thus, the features, advantages and technical effects that are valid for the brain stimulation system and its embodiments and/or the brain stimulation device and its embodiments may also apply to the brain stimulation arrangement and vice versa.

Furthermore, the disclosure relates to a method for treating aphasia. The method may comprise the following steps:

a) providing a task to be performed by a patient to the patient, e.g. the patient suffering from aphasia; and b) stimulating one area or more areas of the patient's brain, e.g. brain language areas involved in language comprehension and/or language production, in a varying current mode, e.g. an alternating current mode, while the patient is performing the task and/or while the task is presented to the patient.

Furthermore, the disclosure relates to a method for treating aphasia. The method may comprise the following steps:

a) providing a task to be performed by a patient to the patient, e.g. the patient suffering from aphasia; and/or b) stimulating one area or more than one area of the patient's brain, e.g. brain language areas involved in language comprehension and/or language production, in a varying current mode, e.g. an alternating current mode, preferably while the patient is performing the task and/or while the task is presented to the patient, wherein preferably a frequency of 75 is used or at least one frequency within the range of 70 Hz to 80 Hz or of 60 Hz to 100 Hz or of 60 Hz to 250 Hz or 70 Hz to 150 Hz.

Furthermore a corresponding device may comprise:

a stimulation functionality which is configured to cause the electronic control unit to issue a stimulation command to an electrical brain stimulation device to cause the electrical brain stimulation device to perform an electrical brain stimulation procedure; and/or a presentation functionality which is configured to cause the electronic control unit to issue a presentation command in order to present a task to be performed by a user on a user interface (110), wherein the stimulation procedure is performed using preferably a frequency of 75 or at least one frequency within the range of 30 to 70 Hz or 70 Hz to 80 Hz or of 60 Hz to 100 Hz or of 60 Hz to 250 Hz or 70 Hz to 150 Hz.

The method may use the brain stimulation system or its embodiments or the brain stimulation device or its embodiments or the brain stimulation arrangement as discussed above. Thus, the features, advantages and technical effects that are valid for the brain stimulation system, the brain stimulation device or the brain stimulation arrangement and their embodiments may also be valid for the method for treating aphasia and vice versa.

The making and using of the presently preferred embodiments are discussed in detail below. It should be appreciated, however, that the present disclosure provides many applicable concepts that can be embodied in a wide variety of specific contexts. The specific embodiments discussed are merely illustrative of specific ways to make and use the disclosed concepts, and do not limit the scope of the claims.

Moreover, same reference signs refer to same technical features if not stated otherwise. As far as "may" is used in this application it means the possibility of doing so as well as the actual technical implementation. The present concepts of the present disclosure will be described with respect to preferred embodiments below in a more specific context namely a brain stimulation arrangement for treating aphasia. The disclosed concepts may also be applied, however, to other situations and/or arrangements as well.

The foregoing has outlined rather broadly the features and technical advantages of embodiments of the present disclosure. Additional features and advantages of embodiments of the present disclosure will be described hereinafter, e.g. of the subject-matter of dependent claims. It should be appreciated by those skilled in the art that the conception and specific embodiments disclosed may be readily utilized as a basis for modifying or designing other structures or processes for realizing concepts which have the same or similar purposes as the concepts specifically discussed herein. It should also be recognized by those skilled in the art that equivalent constructions do not depart from the spirit and scope of the disclosure, such as defined in the appended claims.

The proposed method and its embodiments may not be used for treatment of the human or animal body by surgery or therapy and may not be a diagnostic method practiced on the human or animal body. Alternatively, the proposed method and its embodiments may be used for treatment of the human or animal body by surgery or therapy and may be a diagnostic method practiced on the human or animal body.

Figure 2:
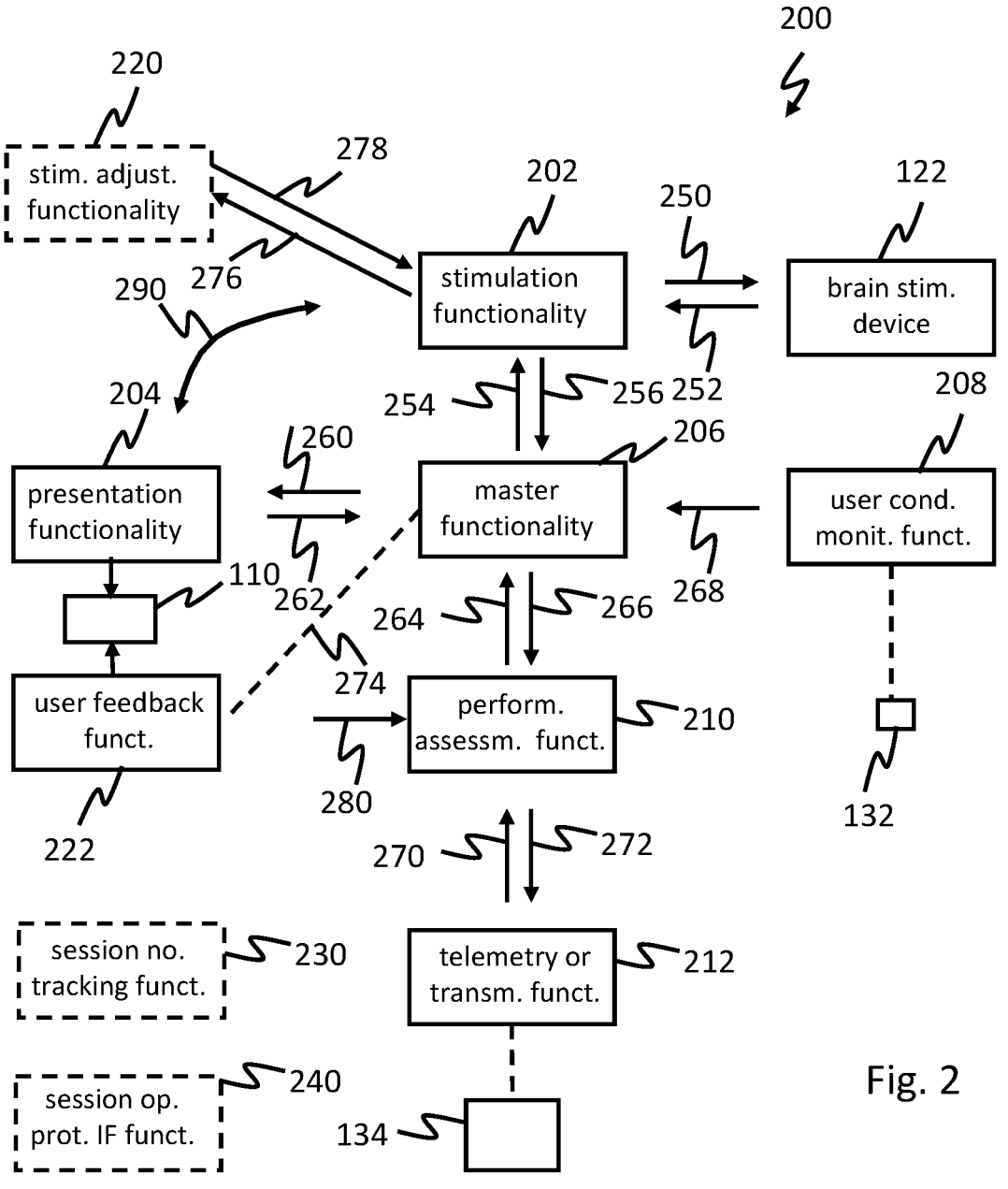
Figure 3A:
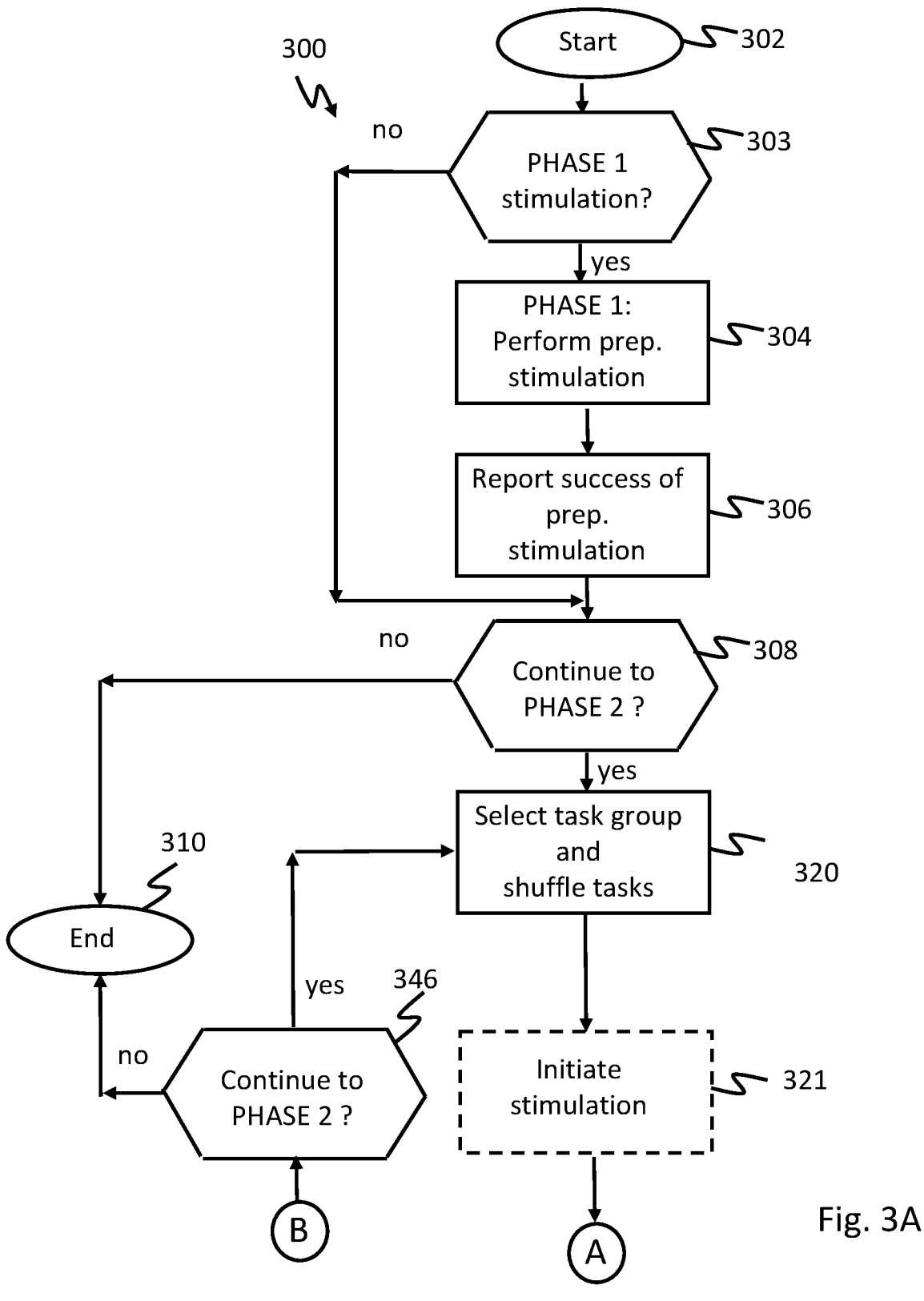
Figure 3B:
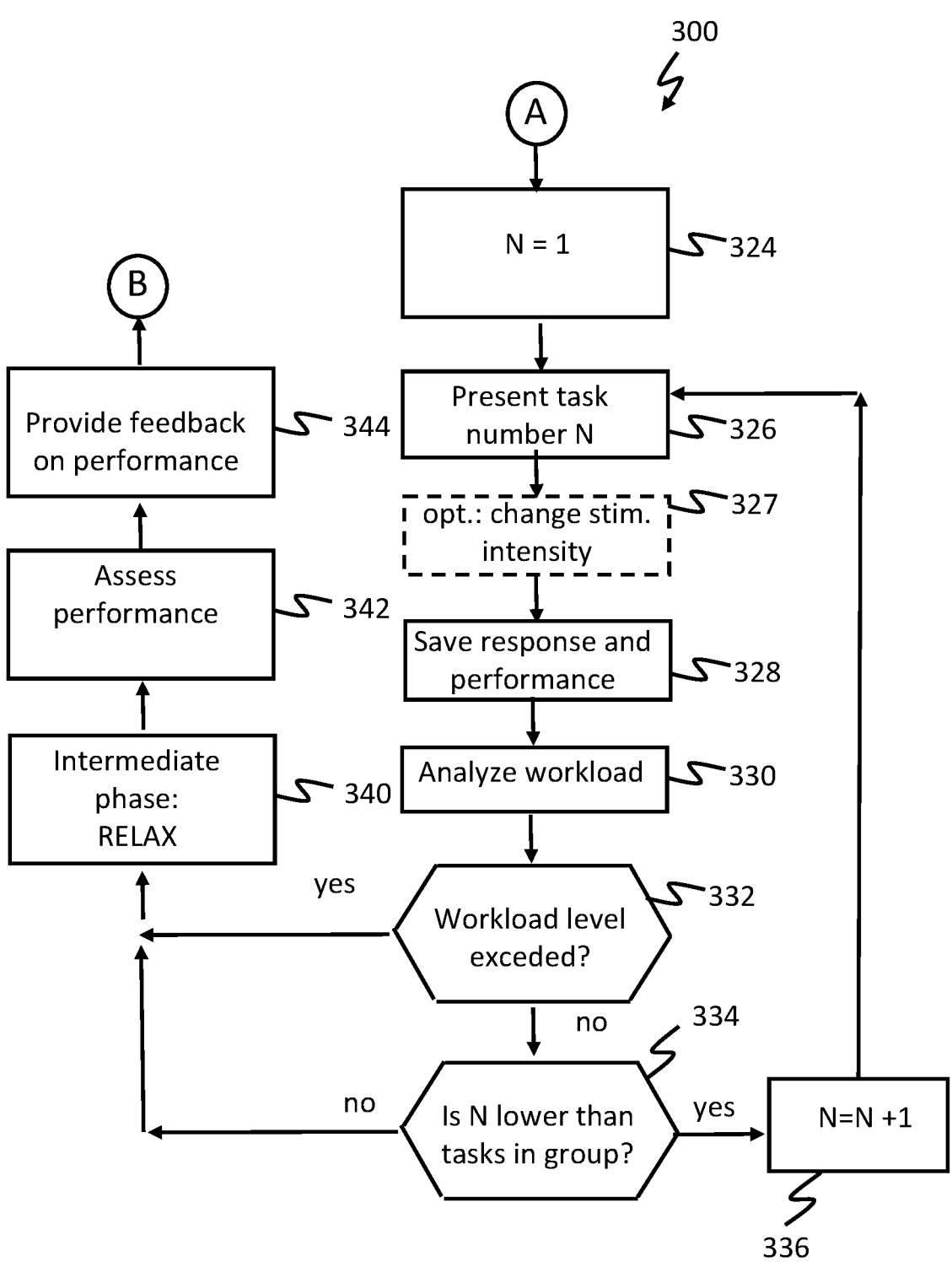
Figure 4:
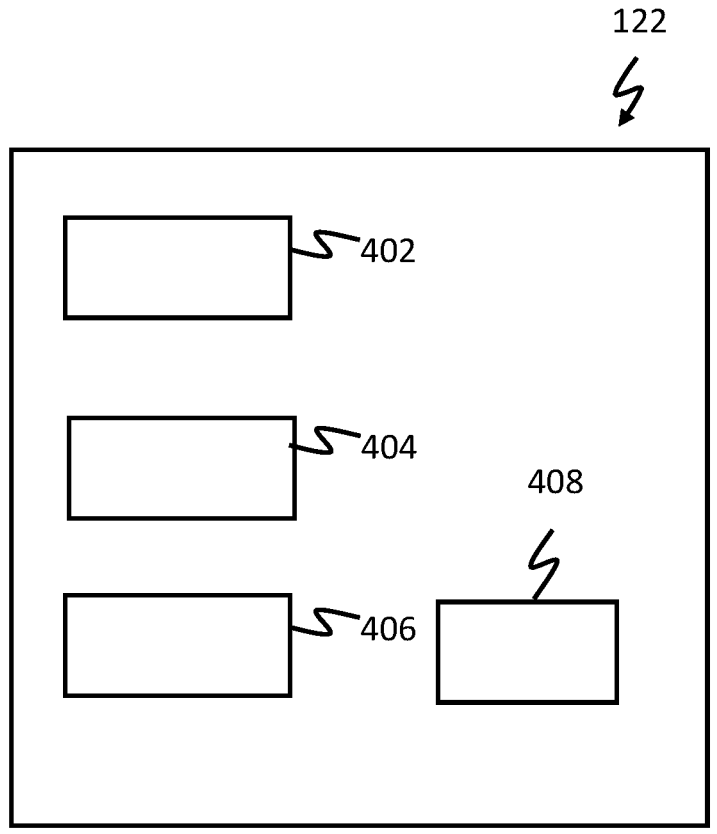

For a more complete understanding of the presently disclosed concepts and the advantages thereof, reference is now made to the following description in conjunction with the accompanying drawings. The drawings are not drawn to scale. In the drawings the following is shown in:

FIG. 1 a brain stimulation arrangement,

FIG. 2 an operation control system of the brain stimulation arrangement,

FIGS. 3A and 3B a method which is performed by the operation control system, and FIG. 4 parts of a brain stimulation device.

FIG. 1 illustrates a brain stimulation arrangement 100 which comprises:

a brain stimulation system 102, for instance a tablet, a laptop, a mobile phone, a smartphone, a personal computer, a workstation or some other kind of computing system, a user interface 110, for instance a monitor, a touch screen, for visible and/or audible input and output, a brain stimulation device 122, an optional user condition monitor device 132, and an optional remote location device 134, e.g. at a location that is in a different room and/or visually separated from the room with the user, and/or at a location that has a distance from brain stimulation system 102 of more than 1 km (kilometer) or more than 10 km. The distance may be smaller than 1000 km or any other distance between two locations on planet earth.

Brain stimulation system 102 comprises:

a volatile memory 104, for instance RAM (Random Access Memory), a non-volatile memory 106, an electronic control unit 108, for instance CPU (Central Processing Unit) or MCU (Microcontroller Unit), and further parts that are not shown in detail, e.g. power source.

Non-volatile memory 106 stores a program code P1. Program code P1 comprises a program that realizes functionalities of the brain stimulation system 102. These functionalities are described in more detail below with regard to FIG. 2. Non-volatile memory 106 may be a SSD (Solid State Disc) memory, a magnetically storing hard disk or some other kind of memory. If the brain stimulation system 102 is switched on, program code P1 is copied as program code P1a and then loaded into volatile memory 104 that allows much faster reading and writing of data than non-volatile memory 106. Electronic control unit 108 performs program code P1a and realizes the functions and functionalities of brain stimulation system 102. Alternatively to a non-volatile memory, the program code P1 may be supplied to the electronic control unit via a data stream.

User interface 110 may be an integral part of the brain stimulation system 102, which may be a smartphone, a mobile phone, a PC (personal computer), work station, a tablet, or a notebook, or it may be a separate device. If user interface 110 is a separate device, there may be a wire connection 112 or a wireless connection between brain stimulation system 102 and user interface 110. Furthermore, a keyboard, a computer mouse or other kinds of input devices may be part of user interface 110, for instance a microphone. User interface 110 may comprise speakers as well. Alternatively or additionally, earphones and/or a microphone may be comprised by or operatively connectable to the brain stimulation device 122 or the user interface 110 for speech input and/or output.

A user 120 or more specifically a patient, e.g. suffering from aphasia, or another person wears the brain stimulation device 122 on his or her head to enable electrical stimulation of their brain 130. Relevant for the treatment of aphasia are especially areas of the brain that play a role for language processing, e.g. language comprehension and/or production, for instance the Wernicke area and/or the Broca area. Brain stimulation device 122 may be operatively connectable or connected to brain stimulation system 102, e.g. by a wired or by wireless connection 124. Details of brain stimulation device 122 are shown in FIG. 4 and are described below.

User condition monitor device 132 may be a device that may have the form of bracelet or a watch and/or that may be carried around the wrist. User condition monitor device 132 may comprise a device that measures EDA, i.e. Electro Dermal Activity, of the skin of user 132. Alternatively or additionally, user condition monitor device 132 may include a device for measuring the pulse of a user 120 that corresponds to the heart beat of user 120. Alternatively or additionally, the heart rate variability (HRV) may also be detected or measured. Functionalities of brain stimulation system 102 may use measurement data of user condition monitor device 132, in particular related to the physiological parameters described above, which may give insight into the current cognitive load experienced by the user. This is explained in more detail below, see user condition monitoring functionality 208 shown in FIG. 2. There may be a wire connection or a wireless connection between user condition monitor device 132 and brain stimulation device 122 and/or brain stimulation system 102.

The remote location device 134 may be used by a person to get remote access to brain stimulation system 102. Remote location device 134 may be a smartphone, a tablet, a laptop, a personal computer etc. There may be a connection between brain stimulation system 102 and remote location device that uses the internet or another communication, e.g. data packet, network. Remote location device 134 may be used for the realization of functionalities of brain stimulation system 102, especially for the realization of a telemetry or transmission functionality 212, see FIG. 2.

FIG. 2 illustrates an operation control system 200 of brain stimulation arrangement 100 of FIG. 1. Operation control system 200 comprises for instance:

a stimulation functionality 202, see section A below, a presentation functionality 204, see section B below, a master functionality 206, see section C below, a user condition monitoring functionality 208, see section D below, a performance assessment functionality 210, see section E below, a telemetry or transmission functionality 212, see section F below, a stimulation adjustment functionality 220, see section I below, a user feedback functionality 222, see section G below, a session number tracking functionality 230, see section H below, and a session operation protocol interface functionality 240, see section J below.

There may be more than these functionalities 202 to 240. Alternatively, only some of the functionalities 202 to 240 may be used, for instance any one or any combination of functionalities 202 to 206.

A) Stimulation Functionality 202

Stimulation functionality 202 may be configured to cause electronic control unit 108 to issue a stimulation command to electrical brain stimulation device 122 to cause electrical brain stimulation device 122 to perform an electrical brain stimulation procedure. The electrical brain stimulation procedure is described in more detail below with reference to FIGS. 3A and 3B.

Stimulation functionality 202 may comprise a preparation stimulation functionality for a preparation stimulation and/or a task stimulation functionality for a task stimulation. The preparation stimulation may be configured to be performed, preferably completely, before the first task of a session is presented to user 120. Alternatively or additionally, the task stimulation may be configured to be synchronized with the presentation of the task. The task stimulation may be performed during the presentation of the task to user 120 and/or during the performance of the task by user 120. The type of stimulation may be contained in the stimulation command to be transcranial electrical stimulation in constant current mode (transcranial direct current stimulation (tDCS)) or in varying current mode (e.g. transcranial alternating current stimulation (tACS), transcranial random noise stimulation (tRNS), pulses of current) or a sequence thereof.

The operation control system 200 may be configured such that during the brain training and/or stimulation session at least one stimulation command for varying current mode is issued. This stimulation command may be synchronized with the presentation of a task on the user interface 110. The stimulation command may be a command for a stimulation in the alternating current mode (tACS). The current in alternating current mode may have the same or a similar frequency that is also present in the natural oscillation of neurons in the relevant brain areas, e.g. brain areas that are relevant for language processing and/or production.

The stimulation command may include stimulation data. Alternatively or additionally, the stimulation command may refer to stimulation data that is stored in memory, for instance in memory 104 or 106. Reference is made to the introductory part of this description for the details of the stimulation data and the stimulation parameters that may be comprised in stimulation data, for instance amplitude and frequency of AC current, magnitude of DC current, presence or absence of preparation stimulation, start and duration of electrical brain stimulation, etc.

There may be device related stimulation commands that are specific for brain stimulation device 122. Alternatively or additionally, stimulation commands on a higher level may be used between the functionalities of operation control system 200.

B) Presentation Functionality 204

Presentation functionality 204 may be configured to cause electronic control unit 108 to issue a presentation command or presentation commands in order to present a task to be performed by user 120 on user interface 110. Stimulation functionality 202 and presentation functionality 204 may be linked or linkable to one another.

Stimulation functionality 202 and presentation functionality 204 may be linked by a link (or relation) 290. The link 290 may be a direct link or an indirect link, for instance via one, two, three or all of the relations 254, 256, 260 and 262 that are described in more detail below. The link 290 may for instance stand for "synchronization" and/or "coordination" and/or "dependency". Link 209 may be unidirectional, e.g. from stimulation functionality 202 to presentation functionality 204 only or vice versa from presentation functionality 204 to stimulation functionality 202. Alternatively, link 290 may be a bidirectional link.

C) Master Functionality 206

A master functionality 206 may coordinate and/or synchronize stimulation functionality 202 and presentation functionality 204. Master functionality 206 may be the central functionality of brain stimulation system 100, e.g. it may be related to numerous functionalities directly, for instance to stimulation functionality 202, to presentation functionality 204, to user condition monitor functionality 208 and to performance assessment functionality 210. Master functionality 206 may be part of the link 290 or of the relation between stimulation functionality 202 and presentation functionality 204.

Master functionality 206 may collect all relevant data that is generated during the operation of brain stimulation device 100.

D) User Condition Monitoring Functionality 208

Operation control system 200 may comprise a user condition monitoring functionality 208 which is configured to determine, based on user condition data that is indicative for the current condition of user 120 whether the brain training and/or stimulation session is continued, e.g. with the presentation of another task, or whether the brain training and/or stimulation session is stopped or interrupted, e.g. to avoid excessive cognitive load for user 120.

The user condition data may be data that is indicative for the current cognitive load experienced by the user 120 and/or it may comprise data on one or more physiological parameters of user 120 which may be monitored by the system during the brain training and/or stimulation session.

If the brain training and/or stimulation session should be stopped or interrupted, operation control system 200 may be configured to cause electronic control unit 108 to issue a stop session command or an interrupt session command to stop, preferably end, or to interrupt, preferably only temporarily, the brain training and/or stimulation session.

There may be the following possibilities to determine the duration of an interruption:

a duration may be used that has always the same length, for instance a duration of less or equal to 5 minutes, and/or the physiological parameter is or the parameters are again in a normal range, i.e. below thresholds that are set for user 120 or that are user independent, and/or the user signals that he or she is ready to continue.

The user condition may be assessed using a camera. This is also a further method to determine if the user 120 is ready to continue the brain training and/or stimulation session.

The brain training and/or stimulation session may be stopped if a session duration limit is reached. The session duration limit may depend on user 120 or may be user independent. Furthermore, termination of the brain training and/or stimulation session is possible if user condition is too bad and/or if a number of interruptions is higher than a threshold set for user 120 or independent of user 120.

E) Performance Assessment Functionality 210

Operation control system 200 may further comprise a performance assessment functionality 210. Performance assessment functionality 210 may be configured to calculate or to provide task performance data which is indicative for the performance of a task by the user 120, e.g. for the quality of the performance. In other words, performance assessment functionality 210 may gather data. The operational control system 200 may be configured to calculate the task performance data from the gathered data, i.e. the task performance data may be generated by machine, especially by brain stimulation system 102. Alternatively or additionally, task performance data may be entered by a practitioner after the performance of the task has been completed or during the performance of the task. This may be appropriate if the performance can only be evaluated with difficulties automatically by software, e.g. by the operation control system 200. Evaluation may be difficult for tasks which require the patient or user 120 to speak.

The performance assessment functionality 210 may consider at least one, an arbitrarily selected plurality of, or all of the following factors:

1) accuracy of performance of the task; this may be calculated or measured by brain stimulation system 102 in case of written tasks and tasks solution or performance or by therapist or practitioner in case of verbal answers to tasks, 2) duration of performance of the task, 3) score from last assessments or results of standard tests, e.g. feeds from standard scales (for instance feed from Western Aphasia Battery or Progressive Aphasia Severity Scale), 4) stimulation intensity factor during performance, this factor may take into account one, and arbitrarily selected plurality of or all of: presence or absence of preparation stimulation (see phase 1 in FIGS. 3A and 3B), presence or absence of task stimulation (see phase 2 in FIGS. 3A and 3B), as well as optionally intensity of these stimulations or other parameters indicative for the electrical stimulations, 5) level of the task, there may be for instance 100 levels on a scale of 0 to 100. Scale 0 may be the easiest level or the level that is most difficult.

The performance may be given a mark, e.g. on a scale of 0 to 100. The mark may be indicative for the quality, e.g. the accuracy, of the performance. The mark may take into account the number of mistakes, for instance the selection of incorrect words, number of typographical errors etc. The mark may be given manually by a supervisor, e.g. the practitioner or another person, or it may be assessed automatically, e.g. computationally, by system 102. The duration of performance considers how long it has taken for the patient to perform the single task. The duration may be determined or measured automatically by brain stimulation system 102, e.g. by measuring the time between the presentation command and a task completed signal or command which may either be generated automatically by the system 102 or require an input, e.g. by the user, the supervisor or the practitioner. Marks may be given according to ranges of duration that are pre-defined for the specific task. In case of written task solutions the time between the start of the task and the end of writing may be used. The duration may also be used as an indication of a correct answer. The duration may express how easily patient's brain combines words related to a specific task. Each task may have a reference time, for instance based on a mean or average time which a healthy subject requires to perform the task. If the duration time is comparable to the average time it may be possible to select a more difficult task next time. Further factors may be considered for performance assessment as well. A final score may be calculated for each task or for a part of the tasks based on one, more or all of these factors. Performance assessment functionality 210 may calculate the following after a full brain stimulation and/or training session (see phase 2 in FIGS. 3A and 3B) session:

a medium or average score across all tasks of session; this may be used to give feedback of the progress of therapy, especially for the therapist or as motivation for user 120, and/or a medium or average score for each type of task; this may be used for detailed reports and/or for adjusting stimulation for different kinds of tasks.

The relevant tasks for performance assessment may be primarily the tasks that require activity of treated brain regions.

F) Telemetry or Transmission Functionality 212

Operation control system 200 may comprise a telemetry or transmission functionality 212 which is configured to transmit session data acquired or generated during the brain training and/or stimulation session to a remote location device 134, such as to a remote computer or a data storage. The session data may comprise one of, any arbitrarily selected plurality of, or all of:

user-specific performance data, e.g. task-specific performance data and/or overall performance data, stimulation-specific data, e.g. comprising data on whether a stimulation procedure such as a preparation stimulation and/or a task stimulation has been performed during the brain training and/or stimulation session and/or data on the stimulation parameters used for the stimulation procedure or stimulation procedures, user condition-specific data, e.g. comprising a user condition data log over the entire brain training and/or stimulation session, user-specific data, e.g. comprising information on the user which is or was subject to the brain training and/or stimulation session, task-specific data, e.g. comprising information on what tasks have been presented, on the difficulty of the task, on the time it took the user to complete the task, and/or on the quality of the performance of the specific task by user 120, and/or session-specific data, e.g. session duration, number of tasks presented during the session, and/or whether the session has been completed as planned or has been interrupted or stopped before its completion.

Telemetry or transmission functionality 212 may be configured to transmit the session data during the brain training and/or stimulation session or only thereafter, e.g. after the last stimulation procedure of the session has been performed and/or after the last task of the session has been presented to the user 120. It is also possible to transmit the data during the session and after the session. Telemetry or transmission functionality 212 may be important for billing and/or accounting a service that is supplied by brain stimulation system 100. More details with regard to billing are explained in section H below.

G) User Feedback Functionality 222

A user feedback functionality 222 may be part of operation control system 200. User feedback functionality 222 may be configured to cause the electronic control unit 108 to issue a feedback command in order to present a feedback to user 120, e.g. on the user interface 110. The feedback or the feedback command may be based on user-specific performance data related to user 120. The feedback may comprise one of, any arbitrarily selected plurality of, or all of:

a feedback to user 120 during the brain training and/or stimulation session, a feedback at the end of the brain training and/or stimulation session after the last task has been presented, and/or a feedback at the beginning of a subsequent brain training and/or stimulation session, e.g. before the first task is presented and/or before the first stimulation procedure is performed.

The respective feedback may be a performance-indicative and/or performance-dependent feedback, e.g. associated with the performance of a specific task and/or with the overall performance of tasks during the brain training and/or stimulation session. Feedback may be very important for motivation of user 120, e.g. because it influences the emotional state of the brain, especially of the limbic system. The emotional state may also affect the language processing skills.

H) Session Number Tracking Functionality 230

A session number tracking functionality 230 of brain stimulation system 102 may be configured to track or count the number of brain training and/or stimulation sessions which have been initiated, completed and/or stopped. When the number of sessions has reached a predetermined maximum, the operation control system 200 may be configured to prevent initiation of a subsequent brain training and/or stimulation session. This function may also play a key role for billing and/or accounting the service that is supplied by brain stimulation system 100.

The brain stimulation system 102 and/or the software that is comprised in brain stimulation system 102 may be distributed as service. It is possible to use a prepaid service for a fixed number of sessions. Session number tracking functionality 230 will count up the number of sessions and may block the further use of the system if the number exceeds the number of session that have already paid. Other payment systems are possible as well, for instance pay by credit card, etc.

If the further use of brain stimulation system 102 is blocked it may be necessary to involve a practitioner for adjusting or confirming the parameters that are used for stimulation and/or for changing or preserving the task level. After the involvement of the practitioner it may be possible to unlock brain stimulation system 102 again in order to perform further brain training and/or stimulation sessions, for instance by prepaying and or by using other methods of payment.

I) Stimulation Adjustment Functionality 220

Operation control system 200 may further comprise a stimulation adjustment functionality 220 which, e.g. based on user-specific performance data, may be configured to adjust stimulation data for one or more subsequent stimulation procedures during the same brain training and/or stimulation session or for a subsequent brain training and/or stimulation session for the same user.

The stimulation parameters may be changed by the stimulation adjustment functionality 220 or may be maintained by the stimulation adjustment functionality 220 depending on the performance data, especially on relative performance data of user 120 that is compared with performance data of other users.

In order to get best results of the therapy, stimulation intensity may be decreased according to objective factors assessed while performing the tasks with stimulation, see performance assessment functionality 210, e.g. section E above. It is possible to decrease the amplitude and/or the duration of stimulation during the treatment process of aphasia. Stimulation may also occur only during a specific task or during specific tasks, for instance during tasks that are more difficult than other tasks.

Stimulation adjustment functionality 220 may for instance be part of stimulation functionality 202. Alternatively, it may be a separate functionality.

J) Session Operation Protocol Interface Functionality 240

A session operation protocol interface functionality 240 of brain stimulation system 102 may be used to receive, preferably user-specific, session operation data that is used for the brain training and/or stimulation session. Session operation data may comprise one of, any arbitrarily selected plurality of, or all of the following data:

data on whether a preparation stimulation is to be performed during the session, data on whether a task stimulation is to be performed during the session, one or more stimulation parameters for the stimulation procedure which is to be performed or for the stimulation procedures which are to be performed, and/or data on the difficulty of the task or the tasks to be presented.

An authentication procedure may have to be successfully completed by a practitioner who is different from user 120 who is made or will be made subject to the brain training and/or stimulation session in order to get access to the session operation protocol interface functionality 240.

There may be the following relations or connections between functionalities 202 to 240:

a relation 250 between stimulation functionality 202 and brain stimulation device 122 that may be used for instance for transmission of first or lower level stimulation commands and/or stimulation data, a relation 252 between brain stimulation device 122 and stimulation functionality 202 that may be used for instance for transmission of confirmation messages which indicate that lower level stimulation commands have been received and/or are being or have been executed properly, a relation 254 between master control functionality 206 and stimulation functionality 202 that may be used for instance for transmission of first level stimulation commands or higher level stimulation commands and/or stimulation data which may be on a higher protocol level than commands that are transmitted via relation 250, for instance a stop session command, an interrupt session command, etc., a relation 256 between stimulation functionality 202 and master control functionality 206 that may be used for instance for transmission of confirmation messages which indicate that higher level stimulation commands have been received and/or are being or have been executed properly, a relation 260 between master control functionality 206 and presentation functionality 204 that may be used for instance for transmission of presentation commands, for instance also stop session command, interrupt session command, etc., a relation 262 between presentation functionality 204 and master control functionality 206 that may be used for instance for transmission of confirmation messages which indicate that presentation commands have been received and/or are being or have been processed successfully, a relation 264 between performance assessment functionality 210 and master control functionality 206 that may be used for instance for transmission of user-specific performance data which may be transmitted further for instance to stimulation adjustment functionality 220, a relation 266 between master control functionality 206 and performance assessment functionality 210 that may be used for instance for transmission of confirmation messages, a relation 268 between user condition monitoring functionality 208 and master control functionality 206 that may be used for instance for transmission of measured values of physiological parameters of user 120, for instance EDA and/or pulse frequency, blood pressure etc. The values of physiological parameters may be part of user condition-specific-data. User condition monitor device 132 may deliver these data.

a relation 270 between telemetry or transmission functionality 212 and performance assessment functionality 210 that may be used for instance for the confirmation of session data, a relation 272 between performance assessment functionality 210 and telemetry or transmission functionality 212 that may be used for instance for transmission of session data acquired or generated during the brain training and/or stimulation session, a relation 274 between master control functionality 206 and user feedback functionality 222 that may be used for instance for transmission of feedback commands, a relation 276 between stimulation functionality 202 and stimulation adjustment functionality 220 that may be used for transmission of confirmation messages that confirm the receipt of a request to change parameters that are used for the stimulation procedure and/or report the successful change of parameters, and/or a relation 278 between stimulation adjustment functionality 220 and stimulation functionality 202 that may be used for instance for transmission of stimulation parameters that have to be changed, e.g. in a subsequent stimulation command.

There may also be a local input interface 280 which may be used by a practitioner to, e.g. manually, enter data into the operation control system, e.g. regarding the quality of the task performance, for instance during the session or after the session. Local input interface 280 may be at the same place or in the same room where the treatment of user 120 takes place or took place. For remote access remote location device 134 may be used, which is preferably visually connected to the treatment location e.g. by video and/or audio, such as via a camera system.

The relations 250 to 278 may be realized as connections for data transmission between software modules.

FIGS. 3A and 3B illustrate a method 300 which is performed by the operation control system 200 that is shown in FIG. 2. All or only some of the functionalities 202 to 240 are used to perform the steps of method 300. The method starts in step 302 for instance by pressing a button or by selecting a button symbol on user interface 110. This may initiate the brain stimulation and/or training session. When the session is initiated, the user 120 may have the brain stimulation device 122 mounted to his head and, optionally, the user condition monitor device 134 may be operatively connected to the user 120, e.g. at the wrist.

The next method step 303 checks whether a preparation stimulation has to be performed. A preparation stimulation may be necessary for instance at the beginning of the first session or for specific users or patients. A question box may be shown on user interface 110 or session data that is stored in memory 104 or 106 may be used to decide whether a preparation stimulation has to be performed or not. Whether or not the preparation stimulation is performed may be pre-set by the supervisor of the session, e.g. the practitioner or another person.

Method step 304 follows immediately after method step 303 if a preparation stimulation should be performed. A preparation stimulation is made in method step 304. The preparation stimulation may be a stimulation that uses a constant stimulation current for brain 130. However, other ways of stimulation are possible as well, where usually tDCS and/or tRNS is the most suitable stimulation. The preparation stimulation, i.e. the electrical stimulation of brain 130 before the performance of tasks by user 120, may be named as phase 1 of stimulation. However, varying current stimulation, e.g. alternating current stimulation or pulsed current is also possible during phase 1 in addition (preferably applied in sequence, i.e. not at the same time) or instead of constant current stimulation. Phase 1 may use anodal stimulation in order to stimulate the relevant areas, e.g. to raise the activity of neurons.

After the end of preparation stimulation; method 300 continues with an optional method step 306. In method step 306 the success of the preparation stimulation is reported, for instance on user interface 110 or in a log file that is stored in memory 104 or 106. The method is performed with the next method step 308 after the reporting.

Method step 308 follows immediately after method step 303 if no preparation stimulation has to be performed, i.e. method steps 304 and 306 are not performed in this case. No preparation stimulation may be possible in another example of method 300. Alternatively, the preparation stimulation may always be performed. This means that step 303 is optional.

Method step 308 checks whether a main stimulation has to be performed, i.e. a stimulation during the performance of tasks that may be called a phase 2 stimulation. The part of a session that uses phase 2 stimulation may be referred to as brain training and/or stimulation session. The whole session may be named as brain training and/or stimulation session even if phase 1 is included at the beginning of the session. The term session may refer to a treatment that is performed on a specific day and/or while the user is continuously wearing the brain stimulation device 122. Many sessions may form a series of session for treatment of aphasia of user 120. The maximum duration of one brain training and/or stimulation session may be limited, e.g. to 60 minutes or to 45 minutes or less. Times for pauses and/or for configurations may not be included within these values.

A question box may be shown on user interface 110 or session data that is stored in memory 104 or 106 may be used to decide whether phase 2 has to be performed. If it is decided that no phase 2 has to be performed a method step 310 follows immediately after method step 308. The method is terminated in method step 310, for instance by switching off brain stimulation system 102 or by starting a new session for another user. This means that it is possible to perform only phase 1 for special users. However, the main application of the brain stimulation system 102 uses phase 2 after phase 1 or only phase 2. Phase 2 may use varying current stimulation. In all cases specified in the foregoing, cathodal stimulation may be used in phase 1 and/or phase 2. Alternatively, phase 1 and/or phase 2 may also use anodal stimulation.

There may be another embodiment that allows the performance of phase 2 without electrical brain stimulation, i.e. only by performing the task or tasks of a session. The evaluation of the results may be relevant for a decision whether electrical brain stimulation shall be used during the next session again.

With regard to the embodiment shown in FIGS. 3A and 3B, a method step 320 follows immediately after method step 308 if it is decided that phase 2 has to be performed. A task group is selected in method step 320. The selection of the task group may be done manually by a practitioner or automatically based on data, e.g. data that has been approved or was input by a practitioner. It is possible to shuffle the tasks in a random manner to make sure that there is alternation, i.e. not too much routine, for user 120. However, shuffling may be optional. In this case, the sequence of tasks presented during the session may be fixed as may be the specific tasks which are presented.

Optional method step 321 follows after method step 320 if the electrical stimulation procedure is only dependent on the task group but not on single tasks. Method step 327 is relevant for electrical stimulation on task level. For stimulation on task group level, the stimulation procedure is started in method step 321, for instance by generation stimulation commands that are described above. The current stimulation may be the same for the whole session disregarding intermediate phases in which the user relaxes. Alternatively the current stimulation may be changed during the session that is under process or that takes place at the moment for user 120, for instance with regard to the kind of current stimulation, with regard to amplitude, frequency, offset, phase etc. A varying current stimulation, especially an alternating current stimulation, may be preferred for phase 2. The frequency of the alternating current, e.g. a sinusoidal current, may correspond to the predominant frequency of oscillations of neurons in the relevant brain area or in the relevant brain areas. Ranges of frequencies and/or for amplitudes that may be used are given in the introductory part above. It is possible to use other forms of signals as well, for instance trapezoid, rectangular, triangular, quadratic, etc. However, constant current stimulation is also possible during phase 2 in addition (preferably applied in sequence, i.e. not at the same time) to varying current stimulation or instead of varying current stimulation. However, varying current stimulation where the variation is adjusted to the brain rhythm may be particularly effective for assisting the brain.

Method step 321 is not performed if the electrical stimulation procedure is dependent on single tasks during a treatment session. In this case method step 327 is performed as described below.

The method is continued in method step 324. In method step 324 a counter is set to a start value. The start value is 1 in the example. However, other start values are also possible, for instance 0.

During the performance of a next method step 326, the task that has the number of the current counter value is presented to user 120, for instance the first task or the first task in the shuffled sequence of tasks. A presentation command may be generated to present the task to user 120. The presentation command may correspond to relation 260 between master functionality 206 and presentation functionality 204.

Method step 327 follows after method step 326 if the stimulation is dependent on the specific task. The brain stimulation system 100 determines the specific stimulation that belongs to the task that was selected in method step 326 using for instance specific data that is stored in memory 104 or 106. The specific stimulation is switched on using appropriate stimulation commands. The current stimulation may be the same for the whole task. Alternatively the current stimulation may be changed during the performance of the task by the user, for instance with regard to the kind of current stimulation, with regard to amplitude, frequency, offset, phase etc. A varying current stimulation, especially an alternating current stimulation, may be preferred for tasks in phase 2. The frequency of the alternating current, preferably a sinusoidal current, may correspond to the predominant frequency of oscillations of neurons in the relevant brain area or in the relevant brain areas. The relevant brain areas may depend on the kind of task. However, constant current stimulation is also possible during phase 2 on task level in addition (preferably applied in sequence, i.e. not at the same time) to varying current stimulation or instead of varying current stimulation. However, varying current stimulation where the variation is adjusted to the brain rhythm may be particularly effective for assisting the brain 130 to solve the tasks.

Method step 327 may not be used if the stimulation procedure is dependent on a task group or selected on a session level. In this case method step 321 is relevant for switching on the electrical brain stimulation.

Method step 328 is performed after method step 326 or alternatively after method step 327. The brain stimulation system 102 saves or stores the responses of user 120 in memory 104 or 106. Furthermore, performance parameters may be stored in memory 104 or 108, for instance the time that the user 120 has needed to perform the current task. The electrical brain stimulation may be switched off in method step 328 if the stimulation is task related.

Brain stimulation system 102 may analyze the workload of user 120 in an optional method step 330. User condition monitor device 132 and user condition monitoring functionality 208 may be used for this purpose, e.g. electro dermal activity (EDA), pulse, and/or heart rate variability.

In a following method step 332, it is checked whether the workload determined from the data acquired by user condition monitor device 132 exceeds a, preferably predefined and/or maximum acceptable, workload level. The threshold for the workload may be defined by a practitioner for a specific user in advance. Alternatively, the user may set a threshold. If the workload level is not exceeded, a method step 334 follows immediately after method step 332.

In method step 334 the brain stimulation system 102 checks whether the current value N of the counter is lower than the number of tasks in the current task group. If yes, method 300 continues with a method step 336.

In method step 336 the value of the counter is incremented, e.g. increased by one. Then, method 300 continues with method step 326 again, i.e. with the presentation of the next task to user 120. Method 300 performs a first loop of method steps 326 to 336. Task by task is presented to user 120 and performed by user 120, for instance writing tasks, reading tasks, association tasks etc. This is repeated until the number of tasks which should be presented is reached.

There may be a monitoring of the duration of the session as well. However, the steps that are relevant for monitoring the duration of the session are not show in FIGS. 3A and 3B in order to not unnecessary complicate the drawings. The duration of the brain training and/or stimulation session may be set in advance before the start of the method 300, for instance using stimulation data and/or session data. If the duration of the session under progress reaches the value that is set in advance the session may be stopped by brain stimulation system 102 independent of the number of tasks that have been solved and independent of the condition of user 120.

Otherwise, a method step 340 follows immediately after method step 334 if the test in method step 334 has the result that the current value N is not lower than the number of tasks within the current task group, i.e. all tasks have been solved. This means that the first loop of method steps 326 to 336 is left.

If the workload level is exceeded in method step 332, method step 340 follows immediately after method step 332, i.e. the first loop is left immediately.

An intermediate phase may take place in method step 340. During method step 340 user 120 relaxes, for instance by closing his or her eyes. The electrical brain stimulation may already have be switched off during method step 328 if it depends on specific tasks. The brain stimulation system 102 may switch off the electrical brain stimulation in method step 340 if it is selected on a task group level. No tasks are presented to user 120 or solved by user 120 during method step 340, i.e. during intermediate phase. Method step 340 may be optional, for instance if the session comprises only one task group.

The intermediate phase may be used to motivate user 120. The brain stimulation system 102 may perform an assessment of the performance of user 120 in a method step 342 in order to prepare the motivation step. The results achieved so far may be displayed to the user 120 and/or the progress which has been achieved may be displayed, e.g. within the intermediate phase. Performance assessment functionality 210 may perform method step 342. Alternatively or additionally a practitioner may support the assessment or make the assessment.

The results of performance assessment may be presented to user 120 in a method step 344. The results may be shown on user interface 110 using graphical representation and/or there may be an audible presentation of the results. It is for instance possible to give the percentage of tasks that have been performed in the current session and/or to highlight improvements with regard to other sessions of the same user 120.

However, method steps 342 and 344 are optional or may be performed only at the end of phase 2, i.e. if all tasks of the session have been performed.

Method 300 continues in a method step 346. Method step 346 checks whether phase 2 has to be continued. Phase 2 is continued in method step 320 if the session comprises a further task group. This means that method 300 is within a second loop that comprises method steps 320 to 346. The second loop may be left in method step 342 if all task groups of the current session have been performed by user 120. A typical duration of a session may be in the range of 20 to 40 minutes, especially without the time for the preparation stimulation, i.e. for performing method steps 302 to 306. As mentioned above, it is also possible to monitor session duration and to terminate method 300 is the session duration exceeds a value that may be set in advance.

It is, of course, possible that one session comprises only one task group. In this case there is no second loop of method steps 320 to 346.

If the check in method step 346 has the result that all tasks have been performed, a method step 310 follows immediately after method step 346. In method step 310 method 300 is terminated. The brain stimulation system 102 may be switched off by user 120 or it may be used for another user or patient.

Method step 346 is also able to check whether the task presentation was interrupted because the check in method step 332 had the result that the workload level was exceeded. It is possible to set a corresponding flag in memory 104 or

108 for that purpose. If the workload was exceeded, i.e. the flag is set, brain stimulation system 102 returns to a method step within the first loop of method steps 326 to 336, for instance by going to method step 334 after the intermediate phase, i.e. after user 120 is relaxed again.

FIGS. 3A and 3B illustrate a flowchart of a computer program product, e.g. software, according to the present disclosure. It will be understood that each block or step of the flowchart and combinations of blocks in the flowchart can be implemented by computer program instructions. These computer program instructions may be loaded onto a data processing unit or another programmable apparatus to form a machine such that the instructions which are executed on the data processing unit or other programmable apparatus create means for implementing the function specified, especially when executed on the the data processing unit or other programmable apparatus, in the blocks or steps of the flowchart. These computer program instructions may also be stored in a computer-readable memory that can direct a data processing unit or other programmable apparatus to function in a particular manner. Moreover, these computer program instructions may be downloaded in e.g. a telecommunications network to cause operational steps to be performed on the data processing unit or other programmable apparatus to produce a computer implemented process such that the instructions which execute on the data processing unit or other programmable apparatus provide steps for implementing the functions specified in the blocks or steps of the flowchart. Accordingly, blocks or steps of the flowchart support combinations of means for performing the specified functions, combinations of steps for performing the specified functions and program instruction means for performing the specified functions. It will also be understood that each block or step of the flowchart and combinations of blocks or steps in the flowchart can be implemented by special purpose hardware-based computer systems which perform the specified function or steps or combinations of the special purpose hardware and computer instructions.

There may be less method steps than shown within FIGS. 3A and 3B. Alternatively there may be more method steps to realize all functions of brain stimulation system 100. Furthermore, the sequence of some of the steps may be changed.

It should be appreciated that the functionalities 202 to 240 that are explained above can be applied in a method of electrically stimulating the brain 130, e.g. for treating aphasia. Thus, references to the computer program product, the operation control system 200, and/or the electronic control unit 108 are advantageous but not necessarily mandatory for the disclosed concepts.

FIG. 4 illustrates parts of the brain stimulation device 122. The brain stimulation device 122 may comprise:

a communication interface 402, a control unit 404, for instance an MCU (Microcontroller Unit) or a CPU (Control Processing Unit), at least one electrode 406 or at least two electrodes 406, preferably three or more electrodes, where, preferably, at least one of the electrodes 406 is configured to be arranged on the head of the user 120 and the other electrode may be placed for instance on an appropriate location of the body of user 120, for instance on his or her shoulder, and an electrical power supply unit 408, for instance a battery or an accumulator.

Communication interface 402 may be a wireless interface, for instance a Bluetooth interface. Stimulation commands may be received from brain stimulation system 102 via communication interface 402, especially via a receiving unit of the interface (not illustrated). The interface 402 may comprise a transmitting unit. Confirmation messages may be sent from communication interface 402 to brain stimulation system 102 using the transmitting unit.

The control unit 404 may control and coordinate the processing of stimulation commands within brain stimulation device 122. The at least two electrodes 406 are connected to appropriate output circuitry. The control unit 404 sends signals or data to this output circuitry according to the stimulation commands. Thus, it is possible to generate constant current output or varying current output at electrodes 406 as desired. A gel may be used to improve current transmission between the electrodes 406 and the cranium and/or brain 130 of user 120. Electrical power supply unit 408 supplies electrical energy to other units of brain stimulation device 122.

In other embodiments, the embodiment that is explained in FIGS. 1 to 4 (e.g. aphasia treating system and method) may use for the optional preparation stimulation and/or for the optional task stimulation:

appropriate frequencies, e.g. as mentioned in the first part of the description that is mentioned before the list of Figures is mentioned, e.g. 17 Hz or e.g. a frequency in the range of 13 Hz (hertz) to 24 Hz or within the range of 12.5 Hz to 30 Hz, alternatively tDCS or tRNS or pulses may be used, and/or appropriate signal levels and durations of applying of the signals to the user may be used, e.g. as mentioned in the first part of the description.

Alternatively, the following frequencies may be used in the embodiment that is explained using FIGS. 1 to 4 (e.g. aphasia treating system and method) as a main stimulation or task stimulation, e.g. see step 321, and/or as a preparation stimulation 304. In particular, the specific examples may comprise the frequency of 75 Hz or a frequency within the range of 70 Hz to 80 Hz or of 60 Hz to 100 Hz or of 60 Hz to 250 Hz or of 30 Hz to 70 Hz or 70 Hz to 150 Hz or 30 Hz to 70 Hz. Alternatively tDCS or tRNS or pulses may be used. Additionally or alternatively to these frequency or frequency ranges, appropriate signal levels and durations of applying of the signals to the user may be used, e.g. as mentioned in the first part of the description.

Both, lower frequency range (e.g. 17 Hz or a frequency from a range of 12.5-30 Hz) and higher frequency range (e.g. 75 Hz or a frequency from a range of 60-250 Hz) may be used during the same treatment session. For instance lower frequency range may be used for preparatory stimulation, while higher frequency range may be used for task stimulation or vice versa. Another embodiment may include using higher frequency range for stimulation of a first brain area (e.g. Wernicke's), and lower frequency range for stimulation of a second brain area (e.g. Broca's) or vice versa, preferably during preparatory stimulation or during task stimulation.

If a preparation stimulation and a task stimulation are used, there may be for instance the following possibilities:

preparation stimulation using higher frequency range for stimulation in first brain area (e.g. Wernicke's) and task stimulation using lower frequency range for stimulation in second brain area (e.g. Broca's), or preparation stimulation using lower frequency range for stimulation in a first brain area (e.g. Wernicke's) and task stimulation using higher frequency range for stimulation in a second brain area (e.g. Broca's), or preparation stimulation using higher frequency range for stimulation in first brain area (e.g. Broca's) and task stimulation using lower frequency range for stimulation in second brain area (e.g. Wernicke's), or preparation stimulation using lower frequency range for stimulation in a first brain area (e.g. Broca's) and task stimulation using higher frequency range for stimulation in a second brain area (e.g. Wernicke's).

Only one, two or more than two (three, four, five etc.) different brain areas may be stimulated in all embodiments that are mentioned above. These different brain areas may be located only on the left side of the brain, only on the right side of the brain or on both sides, i.e. right side and left side.

Although embodiments of the present disclosure and their advantages have been described in detail, it should be understood that various changes, substitutions and alterations can be made therein without departing from the spirit and scope of the disclosure as defined by the appended claims. For example, it will be readily understood by those skilled in the art that many of the features, functions, processes and methods described herein may be varied while remaining within the scope of the present disclosure. Moreover, the scope of the present application is not intended to be limited to the particular embodiments of the system, process, manufacture, method or steps described in the present disclosure. As one of ordinary skill in the art will readily appreciate from the disclosure of the present disclosure systems, processes, manufacture, methods or steps presently existing or to be developed later that perform substantially the same function or achieve substantially the same result as the corresponding embodiments described herein may be utilized according to the present disclosure. Accordingly, the appended claims are intended to include within their scope such systems, processes, methods or steps. Further, it is possible to combine embodiments mentioned in the first part of the description with examples of the second part of the description which relates to FIGS. 1 to 4.

LIST OF REFERENCE SIGNS

100 brain stimulation arrangement
102 brain stimulation system
104 volatile memory
106 nonvolatile memory
108 electronic control unit
110 user interface
112 connection
120 user
122 brain stimulation device
124 wireless connection
P1, P1a program code
130 brain
132 user condition monitor device
134 remote location device
200 operation control system
202 stimulation functionality
204 presentation functionality
206 master functionality
208 user condition monitoring functionality
210 performance assessment functionality
212 telemetry or transmission functionality
220 stimulation adjustment functionality
222 user feedback functionality
230 session number tracking functionality
240 session operation protocol interface functionality
250 to 278 relation
280 local input interface
290 link
300 method 302 to 346 method steps
402 communication interface
404 control unit
406 electrodes
408 electrical power unit

The invention claimed is:

1. A brain stimulation system comprising:
a) a computer program product comprising program code (P1, P1a) which, when loaded and executed on an electronic control unit, provides an operation control system, or
b) an electronic control unit with a program code (P1, P1a) loaded on the electronic control unit, wherein the program code (P1, P1a), when executed on the electronic control unit, provides an operation control system, wherein the operation control system is configured to control a brain training and stimulation session for a brain, wherein the brain training and stimulation session comprises a task performance and a stimulation of the brain, and wherein the operation control system comprises a plurality of control system functionalities, the control system functionalities comprising:
a stimulation functionality which is configured to cause the electronic control unit to issue a stimulation command to an electrical brain stimulation device to cause the electrical brain stimulation device to perform an electrical brain stimulation procedure; and
a presentation functionality which is configured to cause the electronic control unit to issue a presentation command in order to present a task to be performed by a user on a user interface,
wherein the task is presented during the brain training and stimulation session, wherein the operation control system comprises a user condition monitoring functionality which is configured to determine based on user condition data indicative for the current cognitive load/workload experienced by the user during the brain training and stimulation session whether the task performance and the stimulation of the brain training and stimulation session is continued or whether the task performance and the stimulation of the brain training and stimulation session is interrupted only temporarily to avoid excessive cognitive load/workload for the user,
wherein the system is configured such that in case of a temporary interruption, no task is presented to the user by the brain stimulation system, and
wherein a duration of the temporary interruption is determined by at least one physiological parameter of the user being again in a normal range.

2. The brain stimulation system of claim 1,
wherein the stimulation functionality comprises a preparation stimulation functionality for a preparation stimulation and/or a task stimulation functionality for a task stimulation,
wherein the preparation stimulation is configured to be performed before the task is presented to the user and/or the task stimulation is configured to be synchronized with the presentation of the task.

3. The brain stimulation system of claim 2,
wherein the type of stimulation in the stimulation procedure is specified in the stimulation command to be transcranial alternating current stimulation mode,
wherein the frequency of the transcranial alternating current stimulation is in the range of 70 Hz (Hertz) to 80 Hz.

4. The brain stimulation system of claim 3, wherein the frequency is 75 Hz.

5. The brain stimulation system of claim 1,
wherein the operation control system is configured such that, during the brain training and stimulation session, at least one stimulation command for varying current mode is issued in synchronization with the presentation of a task on the user interface.

6. The brain stimulation system of claim 1,
wherein the operation control system is configured such that, during the brain training and stimulation session, a plurality of presentation commands is issued to present different tasks on the user interface during the brain training and stimulation session but only one preparation stimulation is performed.

7. The brain stimulation system of claim 1,
wherein the presentation functionality is configured to select the task to be presented on the user interface from a plurality of tasks of different levels of difficulty, wherein the level of difficulty of the task to be presented is selected by the presentation functionality based on presentation data provided to or calculated by the operation control system.

8. The brain stimulation system of claim 1,
wherein the operation control system comprises a performance assessment functionality, wherein the performance assessment functionality is configured to calculate or to provide task performance data which is indicative of the performance of a task by the user,
wherein the performance assessment functionality considers at least one or both of the following:
accuracy of performance of the task,
duration of performance of the task.

9. The brain stimulation system of claim 8,
wherein the operation control system comprises a user feedback functionality, which is configured to cause the electronic control unit to issue a feedback command in order to present a feedback to the user, wherein the feedback or the feedback command is based on the user-specific performance data related to the user, wherein the feedback is one of, any arbitrarily selected plurality of, or all of:
a feedback to the user during the brain training and stimulation session,
a feedback at the end of the brain training and stimulation session after the last task has been presented, and/or
a feedback at the beginning of a subsequent brain training and stimulation session,
wherein the respective feedback is performance-indicative and/or performance-dependent feedback.

10. The brain stimulation system of claim 8, wherein the performance assessment functionality considers the number of mistakes.

11. The brain stimulation system of claim 10, wherein the performance assessment functionality considers at least one of:
the selection of incorrect words,
the number of typographical errors.

12. The brain stimulation system of claim 8, wherein the duration of performance of the task considers how long it has taken for the user to perform a single task.

13. The brain stimulation system of claim 1,
wherein the operation control system further comprises a stimulation adjustment functionality which is configured to adjust stimulation data for one or more subsequent stimulation procedures during the same brain training and stimulation session or a subsequent brain training and stimulation session for the same user.

14. The brain stimulation system of claim 1, wherein the user condition monitoring functionality is configured to determine based on user condition data indicative for the current cognitive load/workload experienced by the user and based on user condition data comprising one or more physiological parameters of the user which are monitored by the brain stimulation system, during the brain training and stimulation session whether the brain training and stimulation session is continued with the presentation of a task, or whether the brain training and stimulation session is stopped or interrupted to avoid excessive cognitive load/workload for the user, wherein, if the brain training and stimulation session should be stopped or interrupted, the operation control system is configured to cause the electronic control unit to issue a stop session command or an interrupt session command to end, or to interrupt the brain training and stimulation session.

15. The brain stimulation system of claim 1, wherein the operation control system comprises a session number tracking functionality which is configured to track or count the number of brain training and stimulation sessions which have been initiated, completed and/or stopped, wherein, when the number has reached a predetermined maximum, the operation control system is configured to prevent initiation of a subsequent brain training and stimulation session;

and wherein the session number tracking functionality is used for billing or accounting the service that is supplied by the brain stimulation system.

16. The brain stimulation system of claim 1, wherein the operation control system comprises a telemetry or transmission functionality which is configured to transmit session data acquired or generated during the brain training and stimulation session to a remote location device, such as to a remote computer or a data storage, wherein the session data comprises one of, any arbitrarily selected plurality of, or all of:

user-specific performance data, stimulation-specific data comprising data on whether a stimulation procedure such as a preparation stimulation and/or a task stimulation has been performed during the brain training and stimulation session and/or data on the stimulation parameters used for the stimulation procedure or stimulation procedures, user condition-specific data comprising a user condition data log over the entire brain training and stimulation session, user-specific data comprising information on the user which is or was subject to the brain training and stimulation session, task-specific data comprising information on what tasks were presented, on the difficulty of the task, and/or on the time it took the user to complete the task, and/or on the performance of the specific task by user, session-specific data, wherein the telemetry or transmission functionality is configured to transmit the session data during brain training and stimulation session or only thereafter.

17. The brain stimulation system of claim 1, wherein the brain stimulation procedure is performed using stimulation data which comprises one, an arbitrarily selected plurality of, or all of the following stimulation parameters:

amplitude and offset of the current signal for the varying current stimulation procedure;

frequency, range of frequencies and/or phase and/or range of phases and/or offset of the current signal for the alternating current stimulation procedure;

presence or absence of an electrical brain preparation stimulation procedure performed in the same stimulation session but before presentation of the task;

magnitude of the current applied in the constant current stimulation procedure;

duration of the electrical brain stimulation procedure;

start of the electrical brain stimulation procedure.

18. The brain stimulation system of claim 1, wherein the operation control system comprises a session operation protocol interface functionality which is configured to receive user-specific session operation data for the brain training and stimulation session, wherein the session operation data comprises one, an arbitrarily selected plurality of, or all of the following data:

data on whether a preparation stimulation is to be performed during the session, data on whether a task stimulation is to be performed during the session, one or more stimulation parameters for the stimulation procedure(s) which is (are) to be performed, data on the difficulty of the task(s) to be presented, wherein in order to get access to the session operation protocol interface functionality an authentication procedure has to be successfully completed by a practitioner different from that user who is made or will be made subject to the brain training and stimulation session.

19. The brain stimulation system of claim 1, wherein the task is a task related to language comprehension and/or language production, and/or wherein the operation control system comprises a control functionality that is part of the link or that forms the link between stimulation functionality and presentation functionality.

20. The brain stimulation system of claim 1, wherein the user condition monitoring functionality is configured to determine based on user condition data comprising one or more physiological parameters of the user which may give indication of the current cognitive load/workload of the user during the brain training and stimulation session whether the brain training and stimulation session is continued or whether the brain training and stimulation session is stopped or interrupted to avoid excessive cognitive load/workload for the user.

21. The brain stimulation system of claim 1, comprising the brain stimulation device configured to stimulate a human brain, electrically and transcranially, wherein the brain stimulation device is configured to be mounted on a head of a user for a brain training and stimulation session, and wherein the brain stimulation device is configured to be operated to stimulate the brain via varying, especially alternating, current stimulation in a varying current mode of operation and/or via constant current stimulation in a constant current mode of operation in a stimulation procedure; wherein:

a) in the alternating current mode of operation, a frequency or range of frequencies of the alternating current used to stimulate the brain is adjusted or adjustable to a frequency which is characteristic for the brain rhythm that occurs while performing a treatment task in an area of the brain which is to be stimulated via alternating current, and/or b) the brain stimulation device further comprises a device controller, wherein the device controller is configured to select the mode of operation-varying current mode of operation or constant current mode of operation—for the stimulation procedure and/or to set one or more stimulation parameters such that the respective stimulation procedure is performed according to the stimulation parameters, and/or c) the brain stimulation device has a wireless interface for operative connection of the device to an electronic control unit, and/or d) wherein, during operation of the brain stimulation device, the device is configured to stimulate, electrically and transcranial, a specific brain area or areas, related to treated function comprising Wernicke's area and/or Broca's area for speech therapy, wherein the respective area or areas can be stimulated via constant current mode and/or varying current mode.

22. A brain stimulation arrangement comprising the brain stimulation system of claim 1 and a user condition monitor device which is configured to monitor one or more physiological parameters indicative for the cognitive load/workload of the user.

23. A brain stimulation system comprising:

a) a computer program product comprising program code (P1, P1a) which, when loaded and executed on an electronic control unit, provides an operation control system, or b) an electronic control unit with a program code (P1, P1a) loaded on the electronic control unit, wherein the program code (P1, P1a), when executed on the electronic control unit, provides an operation control system, wherein the operation control system is configured to control a brain training and stimulation session for a brain, wherein the brain training and stimulation session comprises a task performance and a stimulation of the brain, and wherein the operation control system comprises a plurality of control system functionalities, the control system functionalities comprising:

a stimulation functionality which is configured to cause the electronic control unit to issue a stimulation command to an electrical brain stimulation device to cause the electrical brain stimulation device to perform an electrical brain stimulation procedure; and a presentation functionality which is configured to cause the electronic control unit to issue a presentation command in order to present a task to be performed by a user on a user interface, wherein the task is presented during the brain training and stimulation session, wherein the operation control system comprises a user condition monitoring functionality which is configured to determine based on user condition data indicative for the current cognitive load/workload experienced by the user during the brain training and stimulation session whether the task performance and the stimulation of the brain training and stimulation session is continued or whether the task performance and the stimulation of the brain training and stimulation session is interrupted only temporarily to avoid excessive cognitive load/workload for the user, wherein the system is configured such that in case of a temporary interruption, no task is presented to the user by the brain stimulation system, wherein a cognitive load/workload level is analyzed, wherein it is checked whether a specific cognitive load/workload level is exceeded, and wherein the temporary interruption is provided if the check indicates that the specific cognitive load/workload level is exceeded.

24. The brain stimulation system of claim 23, wherein a cognitive load/workload level is analyzed during the temporary interruption, wherein the duration of the temporary interruption is determined based on determination if at least one physiological parameter of the user is or at least one parameter related to cognitive load/workload of the user is again in a normal range.

25. The brain stimulation system of claim 24, wherein the duration of the temporary interruption is determined based on determination if the at least one physiological parameter is or the at least one parameter related to cognitive load/workload is again below at least one threshold that is set for the user or that is user dependent.

26. A method for treating aphasia, the method comprising the following steps:

a) providing to a patient a task to be performed by the patient, the patient suffering from aphasia; and b) stimulating one area or more areas of the patient's brain areas involved in language comprehension and/or language production, using varying current mode while the patient is performing the task and/or while the task is presented to the patient, further comprising the step of:

using a brain stimulation system comprising:

a) a computer program product comprising program code (P1, P1a) which, when loaded and executed on an electronic control unit, provides an operation control system, or b) an electronic control unit with a program code (P1, P1a) loaded on the electronic control unit, wherein the program code (P1, P1a), when executed on the electronic control unit, provides an operation control system, wherein the operation control system is configured to control a brain training and stimulation session for a brain, wherein the brain training and stimulation session comprises task performance and stimulation of the brain, and wherein the operation control system comprises a plurality of control system functionalities, the control system functionalities comprising:

a stimulation functionality which is configured to cause the electronic control unit to issue a stimulation command to an electrical brain stimulation device to cause the electrical brain stimulation device to perform an electrical brain stimulation procedure;

wherein a frequency of a transcranial alternating current stimulation used for the brain stimulation procedure is in the range of 70 Hz (Hertz) to 80 Hz; and a presentation functionality which is configured to cause the electronic control unit to issue a presentation command in order to present a task to be performed by a user on a user interface, wherein the task is presented during the brain training and stimulation session, wherein the operation control system comprises a user condition monitoring functionality which is configured to determine based on user condition data indicative for the current cognitive load/workload experienced by the user during the brain training and stimulation session whether the task performance and the stimulation of the brain training and stimulation session is continued or whether the task performance and the stimulation of the brain training and stimulation session is interrupted only temporarily to avoid excessive cognitive load/workload for the user, wherein the system is configured such that in case of a temporarily interruption no task is presented to the user by the brain stimulation system, and wherein a duration of the temporary interruption is determined by at least one physiological parameter of the user being again in a normal range.

27. The method according to claim 26, wherein the operation control system comprises a performance assessment functionality, wherein the performance assessment functionality is configured to calculate or to provide task performance data which is indicative for the performance of a task by the user, wherein the performance assessment functionality considers at least one or both of the following:

accuracy of performance of the task, duration of performance of the task, and wherein the operation control system comprises a user feedback functionality, which is configured to cause the electronic control unit to issue a feedback command in order to present a feedback to the user, wherein the feedback or the feedback command is based on the user-specific task performance data related to the user, wherein the feedback is one of, any arbitrarily selected plurality of, or all of:

a feedback to the user during the brain training and stimulation session, a feedback at the end of the brain training and stimulation session after the last task has been presented, and/or a feedback at the beginning of a subsequent brain training and stimulation session, wherein the respective feedback is performance-indicative and/or performance-dependent feedback.

28. The method according to claim 27, wherein the performance assessment functionality considers a number of mistakes.

29. The method according to claim 28, wherein the performance assessment functionality considers at least one of:

a selection of incorrect words, a number of typographical errors.

30. The method according to claim 27, wherein the duration of performance of the task considers how long it has taken for the user to perform a single task.

\* \* \* \* \*